US006392120B1

(12) United States Patent
Broglie et al.

(10) Patent No.: US 6,392,120 B1
(45) Date of Patent: May 21, 2002

(54) MODIFICATION OF STARCH BIOSYNTHETIC ENZYME GENE EXPRESSION TO PRODUCE STARCHES IN GRAIN CROPS

(75) Inventors: Karen E. Broglie, Landenberg; Jonathan Edward Lightner, Airville, both of PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/345,214

(22) Filed: Jun. 30, 1999

Related U.S. Application Data

(60) Provisional application No. 60/094,436, filed on Jul. 28, 1998.

(51) Int. Cl.[7] ........................ C12N 15/82; C12N 15/29; A01H 5/00; C12P 19/04

(52) U.S. Cl. ....................... 800/284; 800/278; 800/285; 800/286; 800/287; 800/320; 800/320.1; 800/320.3; 435/69.1; 435/101; 435/468

(58) Field of Search ................................ 800/278, 284, 800/286, 287, 320, 320.1, 320.3, 285; 435/468, 101, 69.1

(56) References Cited

U.S. PATENT DOCUMENTS 5,824,790 A 10/1998 Keeling et al. ............ 536/23.6

FOREIGN PATENT DOCUMENTS

| | | |
|---|---|---|
| WO | WO 94/09144 | 4/1994 |
| WO | WO 97/20936 | 6/1997 |
| WO | WO 97/22703 | 6/1997 |
| WO | WO 97/26362 | 7/1997 |
| WO | WO 97/44472 | 11/1997 |
| WO | WO 97/45545 | 12/1997 |
| WO | WO 98/14601 | 4/1998 |
| WO | WO 98/44780 | 10/1998 |

OTHER PUBLICATIONS

Kossmann, J. et al., "Transgenic plants as a tool to understand starch biosynthesis." 1995, Carbohydrate Bioengineering, pp. 271–278.*

Nakatani, M. et al., "Relationship between Starch Content and Activity of Starch Synthase and ADP–glucose Pyrophosphorylase in Tuberous Root of Sweet Potato." 1992, Jpn J. Crop Sci., vol. 61 (3), pp. 463–468.*

Denyer, K. et al., "Identification of multiple isoforms of soluble and granule–bound starch synthase in developing wheat endosperm." 1995, Planta, vol. 196, pp. 256–265.*

Knight M.E., et al, Molecular cloning starch synthase I from maize (W64) endosperm and expression in *Escherichia coli, Plant Journal*, 14, 613–622, Jun. 1998.

NCBI2799009, Large–scale Sequencing Analysis of ESTs from Rice Immature Seed, B. H. Nahm et al., 1998.

NCBI2798408, Large–scale Sequencing Analysis of ESTs from Rice Immature Seed, B. H. Nahm et al., 1998.

NCBI2798263, Large–scale Sequencing Analysis of ESTs from Rice Immature Seed, B. H. Nahm et al., 1998.

NCBI2798218, Large–scale Sequencing Analysis of ESTs from Rice Immature Seed, B. H. Nahm et al., 1998.

Chee Harn et al., Isolation of a Starch Synthase cDNA Clone from Maize Inbred Lin W64A, *Plant Physiology* (*Plant Phys.* ), vol. 108, pp. 50, 1995.

Mary E. Knight et al., Molecular Cloning of Starch Synthase 1 from Maize (W64) Endosperm and Expression in *Escherichia Coli, The Plant Journal*, 14(5), pp. 613–622, 1998.

Tadashi Baba et al., Identification cDNA Cloning, and Gene Expression of Soluble Starch Synthase in Rice, *Institute of Applied Biochemistry*, 103, 565–573, 1993.

Alain Buleon et al., Chlamydomonas reinhardtii as a Model Microbial System to Investigate the Biosyntheisis of the Plant Amylopectin Crystal, *Plant Physiol.*, 115, 949–957, 1997.

Hepiing Cao et al., Identification of the Soluble Starch Synthase Activities of Maize Endosperm, *Plant Physiology*, 120, 205–215, May 1999.

Kay Denyer et al., The elongation of amylose and amylopectin chains in isolated starch granules, *The Plant Journal*, 10(6), 1135–1143, 1996.

Anne Edwards et al., A combined reduction in activity of starch synthases II and III of potato has novel effects on the starch of tubers, *The Plant Journal*, 17(3), 251–261, 1999.

Ane Edwards et al., Biochemical and molecular characterizationof a novel starch synthase from potato tubers, *The Plant Journal*, 8(2), 283–294, 1995.

Anne Edwards et al., Evidence That a 77–Kilodalton Protein from the Starch of Pea Embryos is an Isoform of Starch Synthase that is Both Soluble and Granule Bound, *Plant Physiol.*, 112, 89–97, 1996.

Thierry Fontaine et al., Toward an Understanding of the Biogenesis of the Starch Granule, *The Journal of Biological Chemistry*, 268, No. 22, 16223–16230, 1993.

(List continued on next page.)

*Primary Examiner*—David T. Fox

(57) ABSTRACT

The instant invention discloses utilization of a cDNA clone to construct sense and antisense genes for inhibition of starch synthase enzymatic activity in corn. More specifically, this invention concerns a method of controlling the starch fine structure of starch derived from the grain of cereal crops comprising: (1) preparing a chimeric gene comprising a nucleic acid fragment encoding a starch synthase structural gene or a fragment thereof, operably linked in either sense or antisense orientation on the upstream side to a nucleic acid fragment encoding a promoter that directs gene expression in corn endosperm tissue, and operably linked on the downstream side to a nucleic acid fragment encoding a suitable regulatory sequence for transcriptional termination, and (2) transforming cereal crops with said chimeric gene, wherein expression of said chimeric gene results in alteration of the fine structure of starch derived from the grain of said transformed cereal crops compared to the fine structure of starch derived from cereal crops not possessing said chimeric gene.

21 Claims, 8 Drawing Sheets

OTHER PUBLICATIONS

Ming Gao et al., characterization of dull1, a Maize Gene Coding for a Novel Starch Synthase, *American Society of Plant Physiologists*, 10, 399–412, 1998.

Han Ping Guan et al., Differentiation of the Properties of the Branching Isozymes from Maize, *Plant Physiol.*, 102, 1269–1273, 1993.

Chee Harn et al., Isolation and Characterization of the zSSIIa and zSSIIb Starch Synthase cDNA Clones from Maize Endosperm, *Plant Molecular Biology*, 37, 639–649, 1998.

J. Jane et al., Effects of Amylopectin Branch Chain Length and Amylose Content on the Gelatinization and Pasting Properties of Starch, *American Association of Cereal Chemists, Inc.*, 76, No. 5, 629–637, 1999.

Ralf Bernd Klosgen et al., Molecular Analysis of the Waxy Locus of Zea Mays, *Springer–Vering*, 203 , 203–237, 1986.

Qiang Liu et al., Effects of Moisture Content and Different Gelatinization Heating Temperatures on Retrogradation of Waxy–Type Maize Starches, *Elsevier Science Publishers*, 314, 221–235, 1998.

Jacqueline Marshall et al., Identification of the Major Starch Synthase in the Soluble Fraction of Potato Tubers, *The Plant Cell*, 8, 1121–1135, Jul. 1996.

Chen Mu–Forster et al., Physical Association of Starch Biosynthetic Enzymes with Starch Granules of Maize Endosperm, *Plant Physiol.*, 111, 821–829, 1996.

Christine K. Shewmaker et al., Expression of *Escherichia Coli* Glycogen Synthase in the Tubers of Transgenic Potatoes (*Solanum Tuberosum*) Results in a Highly Branched Starch, *Plant Physiol.*, 104, 1159–1166, 1994.

Yong–Cheng Shi et al., The Structure of Four Waxy Starches Related to Gelatinization and Retrogradation, Carbohydrate Res., 227, 131–145, 1992.

A. M. Smith et al., The Synthesis of the Starch Granule, *Annu. Rev. Plant Physiol. Plant Mol. Biol.*, 48, 67–87, 1997.

Alison M. Smith et al., What Controls the Amount and Structure of Starch in Storage Organs, *Plant Physiol.*, 107, 673–677, 1995.

Ken–ichiro Tanaka et al., Structure, Organization, and Chromosomal Location of the Gene Encoding a Form of Rice Soluble Starch Synthase, *Plant Physiol.*, 108, 677–683, 1995.

Nathalie Van den Koornhuyse, Control of Starch Composition and Structure through Substrate Supply in the Monocellular Alga Chlamydomonas Reinhardtii, *The Journal of Biological Chemistry*, 271, No. 27, 16281–16287, 1996.

Richard G. F. Visser, Expression of a Chimaeric Granule-Bound Starch Synthase–GUS Gene in Transgenic Potato Plants, *Plant Molecular Biology*, 17, 691–699, 1991.

* cited by examiner

SEQUENCE LISTING

```
<160> NUMBER OF SEQ ID NOS: 20

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence:PCR  PRIMER

<400> SEQUENCE: 1

aagcttgaat tccacagaat cagggtacag g                               31


<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:PCR PRIMER

<400> SEQUENCE: 2

gaaggactgg cactagactg g                                          21


<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence:PCR PRIMER

<400> SEQUENCE: 3
```

-continued

```
ggatccgaat tctcctttct cagcaaacgg                                   30


<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:PCR PRIMER

<400> SEQUENCE: 4

aagcttgaat tcctgggatt gccacctgaa ttg                               33


<210> SEQ ID NO 5
<211> LENGTH: 2491
<212> TYPE: DNA
<213> ORGANISM: Zea mays

<400> SEQUENCE: 5

agcgcgcccg aggcggcacc ccaccgtcgt agtagaagac acgggacgca cccccgcagc     60

ctcgctcgct cgctcccctc acttcctccc cgcgcgatcc acggccccccg ccccccgcgc    120

tcctgtctgc tctccctctc cgcaatggcg acgccctcgg ccgtgggcgc cgcgtgcctc    180

ctcctcgcgc gggccgcctg gccggccgcc gtcggcgacc gggcgcgccc gcggcggctc    240

cagcgcgtgc tgcgccgccg gtgcgtcgcg gagctgagca gggaggggcc cgcgccgcgc    300

ccgctgccac ccgcgctgct ggcgcccccg ctcgtgcccg gcttcctcgc gccgccggcc    360

gagcccacgg gtgagccggc atcgacgccg ccgcccgtgc ccgacgccgg cctgggggac    420

ctcggtctcg aacctgaagg gattgctgaa ggttccatcg ataacacagt agttgtggca    480

agtgagcaag attctgagat tgtggttgga aaggagcaag ctcgagctaa agtaacacaa    540

agcattgtct ttgtaaccgg cgaagcttct ccttatgcaa agtctggggg tctaggagat    600

gtttgtggtt cattgccagt tgctcttgct gctcgtggtc accgtgtgat ggttgtaatg    660

cccagatatt taaatggtac ctccgataag aattatgcaa atgcatttta cacagaaaaa    720

cacattcgga ttccatgctt tggcggtgaa catgaagtta ccttcttcca tgagtataga    780

gattcagttg actgggtgtt tgttgatcat ccctcatatc acagacctgg aaatttatat    840

ggagataagt ttggtgcttt tggtgataat cagttcagat acacactcct ttgctatgct    900

gcatgtgagg ctcctttgat ccttgaattg ggaggatata tttatggaca gaattgcatg    960

tttgttgtca atgattggca tgccagtcta gtgccagtcc ttcttgctgc aaaatataga   1020

ccatatggtg tttataaaga ctcccgcagc attcttgtaa tacataattt agcacatcag   1080

ggtgtagagc ctgcaagcac atatcctgac cttgggttgc cacctgaatg gtatggagct   1140

ctggagtggg tattccctga atgggcgagg aggcatgccc ttgacaaggg tgaggcagtt   1200

aattttttga aaggtgcagt tgtgacagca gatcgaatcg tgactgtcag taagggttat   1260

tcgtgggagg tcacaactgc tgaaggtgga cagggcctca atgagctctt aagctccaga   1320

aagagtgtat taaacggaat tgtaaatgga attgacatta atgattggaa ccctgccaca   1380

gacaaatgta tcccctgtca ttattctgtt gatgacctct ctggaaaggc caaatgtaaa   1440

ggtgcattgc agaaggagct gggtttacct ataaggcctg atgttcctct gattggcttt   1500

attggaaggt tggattatca gaaaggcatt gatctcattc aacttatcat accagatctc   1560

atgcgggaag atgttcaatt tgtcatgctt ggatctggtg acccagagct tgaagattgg   1620

atgagatcta cagagtcgat cttcaaggat aaatttcgtg gatgggttgg atttagtgtt   1680

ccagtttccc accgaataac tgccggctgc gatatattgt taatgccatc cagattcgaa   1740
```

-continued

```
ccttgtggtc tcaatcagct atatgctatg cagtatggca cagttcctgt tgtccatgca   1800
actgggggcc ttagagatac cgtggagaac ttcaaccctt tcggtgagaa tggagagcag   1860
ggtacagggt gggcattcgc acccctaacc acagaaaaca tgttgtggac attgcgaact   1920
gcaatatcta catacaggga acacaagtcc tcctgggaag ggctaatgaa gcgaggcatg   1980
tcaaaagact tcacgtggga ccatgccgct gaacaatacg aacaaatctt ccagtgggcc   2040
ttcatcgatc gaccctatgt catgtaaaaa aaggaccaaa gtggtggttc cttgaagatc   2100
atcagttcat catcctatag taagctaaat gatgaaagaa aaccccctgta cattacatgg   2160
aaggcagacc ggctattggc tccattgctc caacgtctgc tttggctggc ttgcctcgat   2220
gcaccggcat gcagtgagga atccagtcga acgacagttt tgaaggatag gaaggggagc   2280
tggaagcagt cacgcaggca gcctcgccgt gattcatatg gaacaagctg gagtcagttt   2340
ctgctatgcc actcactgtt taccttaaga ttattacctg tgttgttgtc ctttgctcgt   2400
tagggctgat aacataatga ctcattagaa aatcatgcct cgtttttatt aactgaagtg   2460
gacacttcta cgccaaaaaa aaaaaaaaaa a                                  2491
```

<210> SEQ ID NO 6
<211> LENGTH: 1528
<212> TYPE: DNA
<213> ORGANISM: Zea mays

<400> SEQUENCE: 6

```
atcgatgaag gcccactgga agatttgttc gtattgttca gcggcatggt cccacgtgaa     60
gtcttttgac atgcctcgct tcattagccc ttcccaggag gacttgtgtt ccctgtatgt    120
agatattgca gttcgcaatg tccacaacat gttttctgtg gttaggggtg cgaatgccca    180
ccctgtaccc tgctctccat tctcaccgaa agggttgaag ttctccacgg tatctctaag    240
gcccccagtt gcatggacaa caggaactgt gccatactgc atagcatata gctgattgag    300
accacaaggt tcgaatctgg atggcattaa caatatatcg cagccggcag ttattcggtg    360
ggaaactgga acactaaatc caacccatcc acgaaattta tccttgaaga tcgactctgt    420
agatctcatc caatcttcaa gctctgggtc accagatcca agcatgacaa attgaacatc    480
ttcccgcatg agatctggta tgataagttg aatgagatca atgcctttct gataatccaa    540
ccttccaata aagccaatca gaggaacatc aggccttata ggtaaaccca gctccttctg    600
caatgcacct ttacatttgg cctttccaga gaggtcatca acagaataat gacaggggat    660
acatttgtct gtggcagggt tccaatcatt aatgtcaatt ccatttacaa ttccgtttaa    720
tacactcttt ctggagctta agagctcatt gaggccctgt ccaccttcag cagttgtgac    780
ctcccacgaa taacccttac tgacagtcac gattcgatct gctgtcacaa ctgcaccttt    840
caaaaaatta actgcctcac ccttgtcaag ggcatgcctc ctcgcccatt cagggaatac    900
ccactccaga gctccatacc attcaggtgg caacccaagg tcaggatatg tgcttgcagg    960
ctctacaccc tgatgtgcta aattatgtat tacaagaatg ctgcgggagt ctttataaac   1020
accatatggt ctatattttg cagcaagaag gactggcact agactggcat gccaatcatt   1080
gacaacaaac atgcaattct gtccataaat atatcctccc aattcaagga tcaaaggagc   1140
ctcacatgca gcatagcaaa ggagtgtgta tctgaactga ttatcaccaa aagcaccaaa   1200
cttatctcca tataaatttc caggtctgtg atatgaggga tgatcaacaa acacccagtc   1260
aactgaatct ctatactcat ggaagaaggt aacttcatgt tcaccgccaa agcatggaat   1320
```

-continued ccgaatgtgt ttttctgtgt aaaatgcatt tgcataattc ttatcggagg taccatttaa 1380
atatctgggc attacaacca tcacacggtg accacgagca gcaagagcaa ctggcaatga 1440
accacaaaca tctcctagac ccccagactt tgcataagga gaagcttcgc cggttacaaa 1500
gacaatgctt tgtgttactt tagctcga 1528

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:PCR PRIMER

<400> SEQUENCE: 7
aagcttgaat tcggcacatc gggccttatg g 31

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:PCR PRIMER

<400> SEQUENCE: 8
gtctagtgcc agtccttc 18

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence:PCR PRIMER

<400> SEQUENCE: 9
gagtcacacg cgatggc 17

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:PCR PRIMER

<400> SEQUENCE: 10
ctctccgcca tggcgacgcc ctcggcc 27

<210> SEQ ID NO 11
<211> LENGTH: 1415
<212> TYPE: DNA
<213> ORGANISM: Zea mays

<400> SEQUENCE: 11
catggcgacg ccctcggccg tgggcgccgc gtgcctcctc ctcgcgcggg ccgcctggcc 60
ggccgccgtc ggcgaccggg cgcgcccgcg gcggctccag cgcgtgctgc gccgccggtg 120
cgtcgcggag ctgagcaggg aggggcccgc gccgcgcccg ctgccacccg cgctgctggc 180
gcccccgctc gtgcccggct tcctcgcgcc gccggccgag cccacgggtg agccggcatc 240
gacgccgccg cccgtgcccg acgccggcct gggggacctc ggtctcgaac ctgaagggat 300
tgctgaaggt tccatcgata acacagtagt tgtggcaagt gagcaagatt ctgagattgt 360
ggttggaaag gagcaagctc gagctaaagt aacacaaagc attgtctttg taaccggcga 420
agcttctcct tatgcaaagt ctgggggtct aggagatgtt tgtggttcat tgccagttgc 480

-continued

```
tcttgctgct cgtggtcacc gtgtgatggt tgtaatgccc agatatttaa atggtacctc    540

cgataagaat tatgcaaatg cattttacac agaaaaacac attcggattc catgctttgg    600

cggtgaacat gaagttacct tcttccatga gtatagagat tcagttgact gggtgtttgt    660

tgatcatccc tcatatcaca gacctggaaa tttatatgga gataagtttg gtgcttttgg    720

tgataatcag ttcagataca cactcctttg ctatgctgca tgtgaggctc ctttgatcct    780

tgaattggga ggatatattt atggacagaa ttgcatgttt gttgtcaatg attggcatgc    840

cagtctagtg ccagtccttc ttgctgcaaa atatagacca tatggtgttt ataaagactc    900

ccgcagcatt cttgtaatac ataatttagc acatcagggt gtagagcctg caagcacata    960

tcctgacctt gggttgccac ctgaatggta tggagctctg gagtgggtat tccctgaatg   1020

ggcgaggagg catgcccttg acaagggtga ggcagttaat tttttgaaag gtgcagttgt   1080

gacagcagat cgaatcgtga ctgtcagtaa gggttattcg tgggaggtca caactgctga   1140

aggtggacag ggcctcaatg agctcttaag ctccagaaag agtgtattaa acggaattgt   1200

aaatggaatt gacattaatg attggaaccc tgccacagac aaatgtatcc cctgtcatta   1260

ttctgttgat gacctctctg gaaaggccaa atgtaaaggt gcattgcaga aggagctggg   1320

tttacctata aggcctgatg ttcctctgat tggctttatt ggaaggttgg attatcagaa   1380

aggcattgat ctcattcaac ttatcatacc agatc                              1415
```

<210> SEQ ID NO 12
<211> LENGTH: 2008
<212> TYPE: DNA
<213> ORGANISM: Zea mays

<400> SEQUENCE: 12

```
catggcgacg ccctcggccg tgggcgccgc gtgcctcctc ctcgcgcggg ccgcctggcc     60

ggccgccgtc ggcgaccggg cgcgcccgcg gcggctccag cgcgtgctgc gccgccggtg    120

cgtcgcggag ctgagcaggg aggggcccgc gccgcgcccg ctgccacccg cgctgctggc    180

gcccccgctc gtgcccggct tcctcgcgcc gccggccgag cccacgggtg agccggcatc    240

gacgccgccg cccgtgcccg acgccggcct gggggacctc ggtctcgaac ctgaagggat    300

tgctgaaggt tccatcgata acacagtagt tgtggcaagt gagcaagatt ctgagattgt    360

ggttggaaag gagcaagctc gagctaaagt aacacaaagc attgtctttg taaccggcga    420

agcttctcct tatgcaaagt ctgggggtct aggagatgtt tgtggttcat tgccagttgc    480

tcttgctgct cgtggtcacc gtgtgatggt tgtaatgccc agatatttaa atggtacctc    540

cgataagaat tatgcaaatg cattttacac agaaaaacac attcggattc catgctttgg    600

cggtgaacat gaagttacct tcttccatga gtatagagat tcagttgact gggtgtttgt    660

tgatcatccc tcatatcaca gacctggaaa tttatatgga gataagtttg gtgcttttgg    720

tgataatcag ttcagataca cactcctttg ctatgctgca tgtgaggctc ctttgatcct    780

tgaattggga ggatatattt atggacagaa ttgcatgttt gttgtcaatg attggcatgc    840

cagtctagtg ccagtccttc ttgctgcaaa atatagacca tatggtgttt ataaagactc    900

ccgcagcatt cttgtaatac ataatttagc acatcagggt gtagagcctg caagcacata    960

tcctgacctt gggttgccac ctgaatggta tggagctctg gagtgggtat tccctgaatg   1020

ggcgaggagg catgcccttg acaagggtga ggcagttaat tttttgaaag gtgcagttgt   1080

gacagcagat cgaatcgtga ctgtcagtaa gggttattcg tgggaggtca caactgctga   1140
```

-continued

```
aggtggacag ggcctcaatg agctcttaag ctccagaaag agtgtattaa acggaattgt   1200

aaatggaatt gacattaatg attggaaccc tgccacagac aaatgtatcc cctgtcatta   1260

ttctgttgat gacctctctg gaaaggccaa atgtaaaggt gcattgcaga aggagctggg   1320

tttacctata aggcctgatg ttcctctgat tggctttatt ggaaggttgg attatcagaa   1380

aggcattgat ctcattcaac ttatcatacc agatctcatg cgggaagatg ttcaatttgt   1440

catgcttgga tctggtgacc cagagcttga agattggatg agatctacag agtcgatctt   1500

caaggataaa tttcgtggat gggttggatt tagtgttcca gtttcccacc gaataactgc   1560

cggctgcgat atattgttaa tgccatccag attcgaacct tgtggtctca atcagctata   1620

tgctatgcag tatggcacag ttcctgttgt ccatgcaact gggggcctta gagataccgt   1680

ggagaacttc aaccctttcg gtgagaatgg agagcagggt acagggtggg cattcgcacc   1740

cctaaccaca gaaaacatgt tgtggacatt gcgaactgca atatctacat acagggaaca   1800

caagtcctcc tgggaagggc taatgaagcg aggcatgtca aaagacttca cgtgggacca   1860

tgccgctgaa caatacgaac aaatcttcca gtgggccttc atcgatcgac cctatgtcat   1920

gtaaaaaaag gaccaaagtg gtggttcctt gaagatcatc agttcatcat cctatagtaa   1980

gctaaatgat gaaagaaaac ccctgtac                                      2008


<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:PCR PRIMER

<400> SEQUENCE: 13

aagcttgaat tcgcagtatg ctcgctctgt gc                                   32


<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence:PCR PRIMER

<400> SEQUENCE: 14

ggatccgaat tcggttccac tcgctcatgt cg                                   32


<210> SEQ ID NO 15
<211> LENGTH: 2019
<212> TYPE: DNA
<213> ORGANISM: Zea mays

<400> SEQUENCE: 15

gaattcggat ccttccctct ggggacatag cgcccggagac tgtcctccca gccccgaagc     60

cactgcatga atcgcctgcg gttgacggag attcaaatgg aattgcacct cctacagttg    120

agccattagt acaggaggcc acttgggatt tcaagaaata catcggtttt gacgagcctg    180

acgaagcgaa ggatgattcc agggttggtg cagatgatgc tggttctttt gaacattatg    240

gggacaatga ttctgggcct ttggccgggg agaatgttat gaacgtgatc gtggtggctg    300

ctgaatgttc tccatggtgc aaaacaggtg gtcttggaga tgttgtggga gctttaccca    360

aggctttagc gagaagagga catcgtgtta tggttgtggt accaaggtat ggggactatg    420

tggaagcctt tgatatggga atccggaaat actacaaagc tgcaggacag gacctagaag    480

tgaactattt ccatgcattt attgatggag tcgactttgt gttcattgat gcccctcttt    540
```

-continued tccggcaccg tcaagatgac atatatgggg gaagtaggca ggaaatcatg aagcgcatga 600
ttttgttttg caaggttgct gttgaggttc cttggcacgt tccatgcggt ggtgtgtgct 660
acggagatgg aaatttggtg ttcattgcca atgattggca cactgcactc ctgcctgttt 720
atctgaaggc atattacaga gaccatgggt taatgcagta cactcgctcc gtcctcgtca 780
tacataacat cgcccaccag ggccgtggtc ctgtagatga attcccgtac atggacttgc 840
ctgaacacta ccttcaacat ttcgagctgt acgatcccgt cggtggcgag cacgccaaca 900
tctttgccgc gggtctgaag atggcagacc gggtggtgac tgtcagccgc ggctacctgt 960
gggagctgaa gacagtggaa ggcggctggg gcctccacga catcatccgt tctaacgact 1020
ggaagatcaa tggcatcgtg aacggcatcg accaccagga gtggaacccc aaggtggacg 1080
tgcacctgcg gtcggacggc tacaccaact actccctcga gacactcgac gctggaaagc 1140
ggcagtgcaa ggcggccctg cagcgggagc tgggcctgga agtgcgcgac gacgtgccgc 1200
tgctcggctt catcgggcgt ctggatggac agaagggcgt ggacatcatc ggggacgcga 1260
tgccgtggat cgcggggcag gacgtgcagc tggtgatgct gggcaccggg cgcgccgacc 1320
tggaacgaat gctgcagcac ttggagcggg agcatcccaa caaggtgcgc gggtgggtcg 1380
gkttctcggt gcctatggcg catcgcatca cggcgggcgc cgacgtgctg gtgatgccct 1440
cccgcttcga gccctgcggg ctgaaccagc tctacgcgat ggcatacggc accgtccctg 1500
tggtgcacgc cgtgggcggg ctcagggaca ccgtggcgcc gttcgacccg ttcagcgacg 1560
ccgggctcgg gtggactttt gaccgygccg aggccaacaa gctgatcgag gcgctcaggc 1620
actgcctcga cacgtaccgg aactacgagg agagctggaa gagtctccag gcgcgcggca 1680
tgtcgcagga cctcagctgg gaccacgcgg ctgagctcta cgaggacgtc cttgtcaagg 1740
ccaagtacca gtggtgaacc ctccgccctc cgcatcaata tcttcggttt gatcccattg 1800
tacatcgcgc gtttgacggt ctcggtgaag aacttcatat gcagtgacgc gccgctgggg 1860
tcggtagcag tactatggga ttgcattgag ctgtgtcact atgtgctttc gacaggacag 1920
tagtgaaggt tgtatgcaag tttatttttt tttcattact gatatttgga atgtcaacac 1980
aataaatgaa gctactatgt gtttcgtaaa aaactcgag 2019

<210> SEQ ID NO 16
<211> LENGTH: 1798
<212> TYPE: DNA
<213> ORGANISM: Zea mays

<400> SEQUENCE: 16
tgtacaatgg gatcaaaccg aagatattga tgcggagggc ggagggttca ccactggtac 60
ttggccttga caaggacgtc ctcgtagagc tcagccgcgt ggtcccagct gaggtcctgc 120
gacatgccgc gcgcctggag actcttccag ctctcctcgt agttccggta cgtgtcgagg 180
cagtgcctga gcgcctcgat cagcttgttg gcctcggcrc ggtcaaaagt ccacccgagc 240
ccggcgtcgc tgaacgggtc gaacggcgcc acggtgtccc tgagcccgcc cacggcgtgc 300
accacaggga cggtgccgta tgccatcgcg tagagctggt tcagcccgca gggctcgaag 360
cgggagggca tcaccagcac gtcggcgccc gccgtgatgc gatgcgccat aggcaccgag 420
aamccgaccc acccgcgcac cttgttggga tgctcccgct ccaagtgctg cagcattcgt 480
tccaggtcgg cgcgcccggt gcccagcatc accagctgca cgtcctgccc cgcgatccac 540
ggcatcgcgt ccccgatgat gtccacgccc ttctgtccat ccagacgccc gatgaagccg 600

-continued

```
agcagcggca cgtcgtcgcg cacttccagg cccagctccc gctgcagggc cgccttgcac      660

tgccgctttc cagcgtcgag tgtctcgagg gagtagttgg tgtagccgtc cgaccgcagg      720

tgcacgtcca ccttggggtt ccactcctgg tggtcgatgc cgttcacgat gccattgatc      780

ttccagtcgt tagaacggat gatgtcgtgg aggccccagc cgccttccac tgtcttcagc      840

tcccacaggt agccgcggct gacagtcacc acccggtctg ccatcttcag acccgcggca      900

aagatgttgg cgtgctcgcc accgacggga tcgtacagct cgaaatgttg aaggtagtgt      960

tcaggcaagt ccatgtacgg gaattcatct acaggaccac ggccctggtg ggcgatgtta     1020

tgtatgacga ggacggagcg agtgtactgc attaacccat ggtctctgta atatgccttc     1080

agataaacag gcaggagtgc agtgtgccaa tcattggcaa tgaacaccaa atttccatct     1140

ccgtagcaca caccaccgca tggaacgtgc caaggaacct caacagcaac cttgcaaaac     1200

aaaatcatgc gcttcatgat ttcctgccta cttcccccat atatgtcatc ttgacggtgc     1260

cggaaaagag gggcatcaat gaacacaaag tcgactccat caataaatgc atggaaatag     1320

ttcacttcta ggtcctgtcc tgcagctttg tagtatttcc ggattcccat atcaaaggct     1380

tccacatagt ccccatacct tggtaccaca accataacac gatgtcctct tctcgctaaa     1440

gccttgggta aagctcccac aacatctcca agaccacctg ttttgcacca tggagaacat     1500

tcagcagcca ccacgatcac gttcataaca ttctccccgg ccaaaggccc agaatcattg     1560

tccccataat gttcaaaaga accagcatca tctgcaccaa ccctggaatc atccttcgct     1620

tcgtcaggct cgtcaaaacc gatgtatttc ttgaaatccc aagtggcctc ctgtactaat     1680

ggctcaactg taggaggtgc aattccattt gaatctccgt caaccgcagg cgattcatgc     1740

agtggcttcg gggctgggag gacagtctcc ggcgctatgt ccccagaggg aaggatcc      1798
```

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:PCR PRIMER

<400> SEQUENCE: 17

ccatctccgt agcacacacc                                                  20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:PCR PRIMER

<400> SEQUENCE: 18

gtgccaagga acctcaacag                                                  20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:PCR PRIMER

<400> SEQUENCE: 19

gagggcatc aatgaacaca                                                   20

<210> SEQ ID NO 20
<211> LENGTH: 2248
```

-continued

<212> TYPE: DNA
<213> ORGANISM: Zea mays

<400> SEQUENCE: 20

```
ccatggcgtc ggcggccgtg tcgtcctctt cctccacctt cttcctcgcg ctcgcctccg     60
cctcccccgg gggccgcagg cgggctaggg tcggctcctc gccgttccac accggcgcca    120
gcctgagttt cgcgttctgg gcgccaccgt cgccgccgcg cgcgccccgg gacgcagcgc    180
tggtgcgcgc cgaggctgag gccgggggca aggacgcgcc gccggagagg agcggcgacg    240
ccgccaggtt gccccgcgct cggcgcaatg cggtctccaa acggagggat cctcttcagc    300
cggtcggccg gtacggctcc gcgacgggaa acacggccag gaccggcgcc gcgtcctgcc    360
agaacgccgc attggcggac gttgagatca agtccatcgt cgccgcgccg ccgacgagca    420
tagtgaagtt cccagcgccg ggctacagga tgatccttcc ctctggggac atagcgccgg    480
agactgtcct cccagccccg aagccactgc atgaatcgcc tgcggttgac ggagattcaa    540
atggaattgc acctcctaca gttgaaccat tagtacagga ggccacttgg gatttcaaga    600
aatacatcgg ttttgacgag cctgacgaag cgaaggatga ttccagggtt ggtgcagatg    660
atgctggttc ttttgaacat tatggggaca atgattctgg gcctttggcc ggggagaatg    720
ttatgaacgt gatcgtggtg gctgctgaat gttctccatg gtgcaaaaca ggtggtcttg    780
gagatgttgt gggagcttta cccaaggctt tagcgagaag aggacatcgt gttatggttg    840
tggtaccaag gtatggggac tatgtggaag cctttgatat gggaatccgg aaatactaca    900
aagctgcagg acaggaccta gaagtgaact atttccatgc atttattgat ggagtcgact    960
ttgtgttcat tgatgcccct cttttccggc accgtcaaga tgacatatat gggggaagta   1020
ggcaggaaat catgaagcgc atgattttgt tttgcaaggt tgctgttgag gttccttggc   1080
acgttccatg cggtggtgtg tgctacggag atggaaattt ggtgttcatt gccaatgatt   1140
ggcacactgc actcctgcct gtttatctga aggcatatta cagagaccat gggttaatgc   1200
agtacactcg ctccgtcctc gtcatacata acatcgccca ccagggccgt ggtcctgtag   1260
atgaattccc gtacatggac ttgcctgaac actaccttca acatttcgag ctgtacgatc   1320
ccgtcggtgg cgagcacgcc aacatctttg ccgcgggtct gaagatggca gaccgggtgg   1380
tgactgtcag ccgcggctac ctgtgggagc tgaagacagt ggaaggcggc tggggcctcc   1440
acgacatcat ccgttctaac gactggaaga tcaatggcat cgtgaacggc atcgaccacc   1500
aggagtggaa ccccaaggtg gacgtgcacc tgcggtcgga cggctacacc aactactccc   1560
tcgagacact cgacgctgga aagcggcagt gcaaggcggc cctgcagcgg gagctgggcc   1620
tggaagtgcg cgacgacgtg ccgctgctcg gcttcatcgg gcgtctggat ggacagaagg   1680
gcgtggacat catcggggac gcgatgccgt ggatcgcggg gcaggacgtg cagctggtga   1740
tgctgggcac cgggcgcgcc gacctggaac gaatgctgca gcacttggag cgggagcatc   1800
ccaacaaggt gcgcgggtgg gtcgggttct cggtgcctat ggcgcatcgc atcacggcgg   1860
gcgccgacgt gctggtgatg ccctcccgct tcgagccctg cgggctgaac cagctctacg   1920
cgatggcata cggcaccgtc cctgtggtgc acgccgtggg cgggctcagg gacaccgtgg   1980
cgccgttcga cccgttcagc gacgccgggc tcgggtggac ttttgaccgc gccgaggcca   2040
acaagctgat cgaggcgctc aggcactgcc tcgacacgta ccggaactac gaggagagct   2100
ggaagagtct ccaggcgcgc ggcatgtcgc aggacctcag ctgggaccac gcggctgagc   2160
```

-continued

```
tctacgagga cgtccttgtc aaggccaagt accagtggtg aaccctccgc cctccgcatc    2220

aatatcttcg gtttgatccc attgtaca                                       2248
```

MODIFICATION OF STARCH BIOSYNTHETIC ENZYME GENE EXPRESSION TO PRODUCE STARCHES IN GRAIN CROPS

This application claims benefit of Provisional Application No. 60/094,436, filed Jul. 28, 1998.

FIELD OF THE INVENTION

This invention is in the field of plant molecular biology. More specifically, this invention pertains to the modification of starch biosynthetic gene expression to produce starches in plants and seeds.

BACKGROUND OF THE INVENTION

Starch is a mixture of two polysaccharides, amylose and amylopectin. Amylose is an unbranched chain of up to several thousand α-D-glucopyranose units linked by α-1,4 glycosidic bonds. Amylopectin is a highly branched molecule made up of up to 50,000 α-D-glucopyranose residues linked by α-1,4 and α-1,6 glycosidic bonds. Approximately 5% of the glycosidic linkages in amylopectin are α-1,6 bonds, which leads to the branched structure of the polymer.

Amylose and amylopectin molecules are organized into granules that are stored in plastids. The starch granules produced by most plants are 15–30% amylose and 70–85% amylopectin. The ratio of amylose to amylopectin and the degree of branching of amylopectin affects the physical and functional properties of the starch. Functional properties, such as viscosity and stability of a gelatinized starch determine the usefulness and hence the value of starches in food and industrial applications. Where a specific functional property is needed, starches obtained from various crops such as corn, rice, potatoes or wheat may meet the functionality requirements. If a starch does not meet a required functional property, such as the need for stable viscosity under high temperatures and acidic conditions, the functionality can usually be achieved by chemically modifying the starch. Various types and degrees of chemical modification are used in the starch industry, and the labeling and use of chemically modified starches must meet government regulations.

Within the starch bearing organs of plants, the proportion of amylose to amylopectin and the degree of branching of amylopectin are under genetic control. For example, corn plants homozygous for the recessive waxy (wx) mutation lack a granule-bound starch synthase enzyme and produce nearly 100% amylopectin. Corn plants homozygous for the recessive amylose extender (ae) mutation and uncharacterized modifier genes can reportedly produce starch granules that are approximately 80% to 90% amylose (see U. S. Pat. No. 5,300,145). The dull mutant of corn lacks a starch synthase distinct from that lacking in the waxy lines and has a starch characterized by more amylose and a larger proportion of shorter branches on the amylopectin molecule than normal starch.

Most cereal crops are handled as commodities, and many of the industrial and animal feed requirements for these crops can be met by common varieties which are widely grown and produced in volume. However, there exists at present a growing market for crops with special end-use properties which are not met by grain of standard composition. Most commonly, specialty corn is differentiated from "normal" corn by altered endosperm properties, such as an overall change in the ratio of amylose to amylopectin as in waxy or high amylose corn, an increased accumulation of sugars as in sweet corn, or an alteration in the degree of endosperm hardness as in food grade corn or popcorn (Glover, D. V. and E. T. Mertz (1987) in *Corn: Nutritional Quality of Cereal Grains; Genetic and Agronomic Improvement,* R. A. Olson and K. J. Frey, eds. American Society of Agronomy, Madison Wis., pp. 183–336; Rooney, L. W. and S. O. Serna-Saldivar (1987) Food Uses of Whole Corn and Dry-milled Fractions, in *Corn: Chemistry and Technology,* S. A. Watson and P. E. Ramstead, eds. American Association of Cereal Chemists, Inc., St. Paul, Minn., pp. 399–429). The current invention offers the buyers of specialty grains a source of starch having properties distinct from waxy starch and offers farmers the opportunity to grow a higher value-added crop than normal or waxy corn.

Purified starch is obtained from plants by a milling process. Corn starch is extracted from kernels through the use of a wet milling process. Wet milling is a multi-step process involving steeping and grinding of the kernels and separation of the starch, protein, oil and fiber fractions. A review of the corn wet milling process is given by S. R. Eckhoff (1992) in the *Proceedings of the Fourth Corn Utilization Conference,* June 24–26, St. Louis, Mo., printed by the National Corn Growers Association, CIBA-GEIGY Seed Division and the United States Department of Agriculture. Wheat is also an important source of purified starch. Wheat starch production is reviewed by J. W. Knight and R. M. (1984) Olson in Starch: *Chemistry and Technology* $2^{nd}$ Editition., Academic Press. Eds. Whisler et al.

Starch is used in numerous food and industrial applications and is the major source of carbohydrates in the human diet. Typically, starch is mixed with water and cooked to form a thickened gel. This process is termed gelatinization. Three important properties of a starch are the temperature at which gelatinization occurs, the viscosity the gel reaches, and the stability of the gel viscosity over time. The physical properties of unmodified starch during heating and cooling limit its usefulness in many applications. As a result, considerable effort and cost is needed to chemically modify starch in order to overcome these limitations of starch and to expand the usefulness of starch in industrial applications.

Some limitations of unmodified starches and properties of modified starches are given in *Modified Starches: Properties and Uses,* O. B. Wurzburg, ed., (1986) CRC Press Inc., Boca Raton, Fla. Unmodified starches have very limited use in food products because the granules swell and rupture easily, thus forming weak bodied, undesirable gels. Chemical modifications are used to stabilize starch granules thereby making the starch suitable for thousands of food and industrial applications including baby foods, powdered coffee creamer, surgical dusting powders, paper and yarn sizings and adhesives. Common chemical modifications include cross linking, in which chemical bonds are introduced to act as stabilizing bridges between starch molecules, and substitution in which substituent groups such as hydroxyethyl, hydroxypropyl or acetyl groups are introduced into starch molecules.

The use of chemically modified starches in the United States is regulated by the Food and Drug Administration (FDA). "Food starch-modified" starches may be used in food but must meet specified treatment limits, and "industrial starch-modified" starches may be used in items such as containers that come in contact with food and must also meet specified regulatory requirements; Code of Federal Regulations, Title 21, Chapter 1, Part 172, Food Additives Permitted in Food for Human Consumption, Section 172, 892, Food Starch-Modified, U. S. Government Printing Office, Washington, D.C. 1981; (a) Part 178, Indirect Food Additives, Sect. 178.3520, Industrial Starch-Modified. These regulations limit the degree of chemical modification by defining the maximum amount of chemical reagent that can be used in the modification steps. The levels of by-products in starch resulting from the modification process are also regulated. For example, propylene chlorohydrin residues in hydroxypropyl starch are of special concern (Tuschhoff, J. V. (1986) Hydroxypropylated Starches, in *Modified Starches: Properties and Uses,* O. B. Wurzburg, ed., CRC Press, Boca Raton, Fla., pp. 90–96).

In addition to its use as a purified ingredient, starch is an important component of whole flours, such as wheat flour, used in the production of breads, baked goods and pastas. Starch comprises between 50 and 70% of the weight of a wheat grain and its importance in the performance of wheat flours is well known in the art. Although the complex genetics of wheat has limited the variations in starch fine structure that is available in whole flours, the production of novel starch structures in wheat or other flours may result in improved performance of these whole flours in food product applications. Starch structure is also an important component of the quality of whole consumed cereal grains such as rice. Differences in amylopectin fine structure have been related to cooked rice texture (Reddy et al. (1993) *Carbohydr. Polymers* 22:267–275).

Differences in the degree of starch branching or polymerization are known to result in a change in the physiochemical properties of starch. It has been suggested that starches, tailor-made for specific applications, may be generated by alteration of the branch chain distribution of the amylopectin molecule, the relative proportion of amylose to amylopectin or the degree of polymerization of amylose. Some authors (Shi and Seib (1992) *Carbohydr. Res.* 227:131–145; Jane et al. (1999) Cereal Chemistry In Press), have reported that retrogradation tendency is reduced in starches from different botanical sources which contain increased proportions of very short chains (DP 6–9) in their amylopectin, but no suggestion as to how this might be achieved in corn is made. However, achieving phenotypic alteration of starch composition has been problematic; while key enzymes in starch biosynthesis have been identified, their exact roles remain uncertain. Thus, correlation of activities of particular enzymes with particular molecular characteristics of starch structure and, in turn, with starch function in food and industrial products has been difficult. Although desirable functional properties that an ideal starch might need can be envisioned, there is only a limited understanding of what the molecular structure of the starch should be to achieve this and little understanding of how particular starch biosynthetic enzymes specifically affect those parameters. For example, the role of individual enzymes in determining the branching patterns and length of branches is as yet unclear and is compounded by the lack of understanding of how branching enzymes and starch synthases interact. In addition, while the role of the granule-bound starch synthase encoded by the waxy gene is fairly well understood; see Denyer et al. (1996) *Plant J* 10:1135–1143), the number and exact functions of other starch synthases, soluble or granule-bound, are not well understood. (Smith et al. (1996) *Ann. Rev. Plant Phys. and Mol. Biol.* 48:67–87).

WO 94/09144 discusses the generation of corn plants with improved ability to synthesize starch at elevated temperatures. This publication proposes that the limiting factor in grain filling at elevated temperature is the lability of certain starch biosynthetic enzymes, particularly starch synthase (SS) and starch branching enzyme (SBE). The introduction of genes encoding enzymes that have a higher optimum temperature for activity or that have a higher tolerance to heating into plants may afford an increase in the amount of starch deposited in the corn kernel. Moreover, it is claimed that this strategy may be used to generate starch of altered fine structure as a result of the introduction of donor genes whose expression may alter the balance of the different starch biosynthetic enzymes. Suggested donor genes include those that encode enzymes that display improved kinetic or allosteric properties relative to the endogenous enzyme or an extra copy of the endogenous gene that would compensate for losses in enzyme activity incurred due to heat lability. As a means to alter starch structure, WO 94/09144 also suggests the use of sense and antisense genes to alter the natural ratios of the different starch synthase and branching enzymes in the recipient plant. This publication discloses the effect of temperature on catalytic activity and enzyme stability for certain starch biosynthetic enzymes. However, no data are presented to substantiate the proposed molecular strategies. Indeed, while this publication suggests the use of altered starch synthase expression to alter starch fine structure, both amylose/amylopectin ratios and degree of amylopectin branching, other publications before and after suggest that starch branching enzymes, not just starch synthases, would be required, or that still other factors must be addressed. For example, Smith et al. (1995, *Plant Phys.* 107:673–677) suggest two distinct views about the determination of the branching pattern of amylopectin: first, that the pattern represents a balance between the activities of branching and debranching enzymes, and second, that the pattern can be explained largely by the properties of branching enzymes. No role for starch synthases is provided. Guan and Preiss (1993, *Plant Phys.* 102:1269–1271) suggest a study of the interactions among the multiple forms of branching enzymes and starch synthase may be essential for understanding the specificity and function of the individual isozymes and the mechanism of amylopectin biosynthesis. Thus, Guan and Preiss imply the need to alter both enzymes at once. Lastly, Van den Koornhuyse et al. (1996, *J Biol. Chem.* 271:16281–16287) propose that low nucleotide sugar concentrations are either directly or indirectly responsible for the major differences observed in the composition of structure of starch during storage. In sum, it is clear from the differing views that there is no consensus as to exactly what factors affect starch structure and thus how to alter it. Furthermore, no workers, including WO 94/09144, present evidence demonstrating that soluble starch synthases limit the rate of polymerization and therefore that either increasing or reducing their level will actually alter starch fine structure. WO 94/09144 further does not teach how to differentiate between genes encoding isoforms that make a minimal contribution to starch biosynthesis and more active forms. Reducing the expression pattern of a relatively inactive (at the enzymatic level, not necessarily at the transcriptional level) enzyme is unlikely to have an effect. In sum, WO 94/09144 makes a suggestion but does not teach in sufficient detail for the skilled artisan to actually produce a starch altered in fine structure.

There have been several reports of alteration of starch structure by modification of SBE expression in both potato (Virgin et al. (June, 1994) at the 4$^{th}$ International Congress of Plant Molecular Biology, and Christensen et al. and Kossman et al. (July, 1994) at the Plant Polysaccharide Symposium) and corn (Broglie et al.; WO 97/22703). None of that work addresses the potential of altering the expression of starch synthases. Several authors have speculated that altering non-granule-bound starch synthase I (non-GBSSI) synthase expression would alter starch structure or compostion, but this has not been clearly demonstrated in cereals (Block et al., WO 9745545A; Frohberg and Kossmann, WO 9744472; Frohberg and Kossmann, WO 9726362).

Although the enzymatic steps are known, the molecular details of starch biosynthesis are not well understood. It is not clear whether the different SS isoforms contribute equally throughout starch biosynthesis or whether each isoform plays a distinct role in assembling the amylopectin molecule at discrete steps along an obligatory pathway. In consideration of the possible interplay between the starch branching enzymes and the multiple starch synthases that function in glucan chain elongation, it is impossible to make accurate predictions concerning starch structure based upon the catalytic properties of each enzyme.

Beyond the clear role of GBSSI in amylose biosynthesis, the exact roles of individual starch synthases are not clear. There is evidence from some, but not all, species that individual isoforms of SS make qualitatively different contributions to amylopectin biosynthesis and that GBSSI may also contribute to amylopectin as well as amylose biosynthesis (Smith et al. (1997) *Ann. Rev. Plant Phys. and Mol. Biol.* 48:67–87). Numerous starch synthases have been cloned from different species, but Edwards et al. (1960, *Plant Phys.* 112:89–97), and Mu-Forster et al. (1996, *Plant Phys.* 111:821–829) demonstrated that the previously made distinction between granule-bound and soluble starch synthases may not reflect the in vivo situation and it will not be used here with the exception of the waxy protein, GBSSI. Since its original isolation from corn (Klösgen et al. (1986) *Mol. Gen. Genet. 203:*237–244) this gene has been cloned from many species. Numerous other SS have been cloned from a range of species, but they appear to be less closely related across species than GBSSI. Potato contains at least two other starch synthases, SSII and SSIII (Marshall et al. (1996) *Plant Cell* 8:1121–1135). Pea contains a synthase designated SSII which appears to be present in two forms, one derived by the processing of the other (Edwards et al. (1996) *Plant Phys.* 112:89–97). Block et al. (WO 9745545A) isolated two starch synthase cDNA clones from wheat. Three forms of soluble starch synthase were, purified from rice. These were shown to be derived from a primary form by the isolation of the corresponding gene referred to as soluble starch synthase I (SSSI) (Baba et al. (1993) *Plant Phys.* 103:565–573; Tanaka et al. (1995) *Plant Phys.* 108:677–683). Rice Expressed Sequence Tags (ESTs) showing homology to the starch synthase II sequences of pea and potato have been identified (AA752475, AA753266, AA751702, AA751557, AA751512A; Nahm, B. H. at al.). A sequence related to rice SSI was isolated from corn (Ham et al. (1995) *Plant Phys.* 108:S-50; Keeling et al., WO 9720936) and was designated corn SSI. Two additional starch synthase cDNA clones have been isolated by Keeling et al. (WO 9720936). The expression of the genes encoding these starch synthases has been studied and their representation in the corn genome has been reported (Harn et al. (1998) *Plant Mol. Biol.* 37:639–649). Frohberg and Kossmann (WO 97/44472 and WO 97/26362) have also reported the isolation of two of these corn starch synthase sequences. The locus responsible for the dull mutation in corn was recently shown to encode another starch synthase (Gao et al. (1998) *Plant Cell* 10:399–412). In a study characterizing the soluble starch synthase activities in maize endosperm, Cao et al. (1999) *Plant Physiol.* 120:205–215, report that DU1 and SSI likely account for all of the soluble starch synthase activity in developing endosperm. Unicellular organisms also contain multiple starch synthases (Fontaine et al. (1993) *J Biol. Chem.* 268:16223–16230; Buleon et al. (1997) *Plant Physiol.* 115:949–957). While for some of these enzymes authors have speculated on its particular role, in no case has it been elucidated how the full complement of starch synthase isoforms work together to elongate amylopectin branches or how the entire array of starch biosynthetic enzymes in a particular species interact and function together to produce the starch structure that is observed in the mature seed or tuber. In particular, the role of low abundance starch synthases in endosperm is unclear.

It is well known that the waxy mutation in corn results in the lack of a functional GBSSI enzyme and in altered starch composition. Similarly in wheat, low amylose varieties have been selected which lack the GBSS. Dominant forms of the analogous mutation in potato have been made by expressing GBSSI antisense genes in transgenic potato plants (Visser et al. (1991) *Plant Mol. Biol.* 17:691–699). Shewmaker et al. (1994, *Plant Physiol.* 104:1159–1166) have reported altered starch structure in potato through the expression of *E. coli* glycogen synthase in tubers. Modified expression of non-GBSSI starch synthases have also been reported in potato. Reduction of SSII expression in transgenic potato tubers has been achieved using antisense technology. Decreased levels of SSII protein were not correlated with any detectable change in starch content or composition and starch granule morphology appeared normal (Edwards et al. (1995) *Plant J.* 8:283–294). Recently, small changes in amylopectin branch chain distribution (dp 6–35) have been reported in SSII antisense potato plants (Edwards et al. (1999) *Plant J* 17:251–261). Different results were observed when the major soluble starch synthase activity of potato tubers, SSIII was inhibited by an antisense approach. In these transgenic plants, starch content and composition was not changed, however, starch granule morphology was noticeably affected (Marshall et al. (1996) *Plant Cell* 8:1121–1135). Changes in amylopectin branch chain distribution were also observed but these were distinct from those found in the SSII antisense plants (Edwards et al. (1999) *Plant J* 17:251–261). A pea mutant, rug5 was found to be lacking in a starch synthase isoform that is highly homologous to the SSII of potato. Although the two starch synthases share homology in amino acid sequence, different results were produced when this starch synthase isoform was inhibited in pea. Noticeable changes were apparent in short (dp<15), medium (dp 15–45) and very long (dp~1000) amylopectin branch chains. In addition, these structural changes were associated with gross changes in starch granule morphology. Thus, while transgenic results from potato suggest that within a specific organ, different isoforms of starch synthase perform different roles in starch biosynthesis, results obtained from the pea rug5 mutant indicate that homologous isoforms may not necessarily perform the same function in different starch storing organs. Generalization about the role of specific isoforms and prediction of starch phenotypic changes which accompany modified expression is rendered difficult due to differences in the number of isoforms represented within different organs as well as differences in the relative amounts of activity contributed by the different isoforms. While transgenic work aimed at the modification of starch synthase expression has been reported in potato, no similar experiments have been described in corn.

U.S. Pat. No. 5,824,790 reports the isolation and sequence of 3 non-waxy starch synthase cDNA clones from maize. It suggests the use of these sequences to generate constructs designed to modify expression of these starch synthases in transgenic plants. It further suggests that modified protein expression may give rise to a change in the fine structure of the starch. While the nucleotide and protein sequences for the 3 starch synthases are provided, no data are given concerning the generation and characterization of transgenic plants carrying DNA constructs derived from these sequences; similarly no data relating to starch composition and structure in transgenic plants is reported. In the absence of specific roles for the different isoforms of soluble starch synthase in cereal endosperm, and with the presence of activities for the SSIIa and SSIIb class enzymes in endosperm in question, (Cao et al. (1999) *Plant Physiol.* 120:205–215) it is clear that gene sequences alone provide no clear indication of what type of change, if any, to starch structure may be accomplished by altering the expression of a particular soluble starch synthase gene. And in the absence of this predictive power or the actual production of the starch the utility of any given change is unclear. In fact, in terms of specific functional attributes such as retrogradation tendency it is clear that some starch structural changes are actually detrimental to utility. Qiange and Thompson (1998, *Carbohydr. Res.* 314:221–235) examined retrogradation of three double mutants of maize, duwx, aewx and su2wx, in comparison to normal waxy starch and showed increased retrogradation tendency in two of the three amylopectin types. Thus, it is clear that change alone is insufficient to improve the utility of cereal straches, and that some changes may be improvements while others are neutral or even detrimental. In the absence of the ability to meaningfully predict the structural change that can be produced with a given genetic modification the only way to identify useful changes is to actually produce the modified starch.

Molecular genetic solutions to the generation of starches from cereal crops with altered fine structures have a decided advantage over more traditional plant breeding approaches. Changes to starch fine structure can be produced by specifically inhibiting expression of one or more of the SS or SBE isoforms by antisense inhibition or cosuppression (WO 94/09144). An antisense or cosuppression construct would act as a dominant negative regulator of gene activity. While conventional mutations can yield negative regulation of gene activity these effects are most likely recessive. The dominant negative regulation available with a transgenic approach may be advantageous for certain grain production methods. In addition, the ability to restrict the expression of the altered starch phenotype to the reproductive tissues of the plant by the use of specific promoters may confer agronomic advantages relative to conventional mutations which will have an effect in all tissues in which the mutant gene is ordinarily expressed. Finally, the variable levels of antisense inhibition or cosuppression that arise from chromosomal position effects could produce a wider range of starch phenotypes than those that result from dosage effects of a mutant allele in cereal endosperm.

The incomplete understanding of the role of different starch synthase enzymes in cereal crops render attempts to manipulate starch fine structure by inhibition of starch synthase gene expression difficult. However, manipulation of starch synthase enzyme gene expression by cosuppression and antisense technology is possible and would likely produce a desirable phenotype. Thus, one of ordinary skill in the art only has to screen multiple transgenic plants for the desired alteration in starch fine structure.

SUMMARY OF THE INVENTION

The instant invention discloses utilization of cDNA clones to construct chimeric sense and antisense genes for alteration of starch synthase enz:ymatic activity in corn grain or endosperm and the grain or endosperm of other cereal crops. More specifically, this invention concerns a method of producing a transformed cereal crop wherein the starch fine structure derived from a grain of the cereal crop is altered compared to the fine structure of starch derived from a non-transformed cereal crop comprising: (1) preparing a chimeric gene comprising a nucleic acid fragment encoding a non-GBSSI starch synthase enzyme structural gene or a fragment thereof, operably linked in either sense or antisense orientation on the upstream side to a nucleic acid fragment encoding a promoter that directs gene expression in endosperm tissue, and operably linked on the downstream side to a nucleic acid fragment encoding a suitable regulatory sequence for transcriptional termination, and (2) transforming cereal crops with said chimeric gene, wherein expression of the chimeric gene results in alteration of the fine structure of starch derived from the grain of the transformed cereal crops compared to the fine structure of starch derived from cereal crops not possessing said chimeric gene. The invention also concerns a method of producing a transformed cereal crop wherein the starch fine structure derived from a grain of the cereal crop has a change in the relative proportions of amylose to amylopectin relative to that of starch derived from cereal crops not possessing the chimeric gene above, or a change in the degree of polymerization of the amylose component of starch derived from the transformed cereal crop relative to the degree of polymerization of the amylose of starch derived from cereal crops not possessing the chimeric gene above. To date no reports have demonstrated an alteration in molecular structure of starch created by altering the expression level of non-GBSSI starch synthase in a transgenic plant. This invention describes the specific alterations in starch structures, changes in amylose to amylopectin ratio, changes in amylopectin fine structure, increased abundance of very short amylopectin chains (DP 6–9), and change in the degree of polymerization of amylose, that can be created by controlling the expression of non-GBSSI starch synthases in transgenic plants.

This invention also concerns cereal crop varieties prepared by transformation using said method, starch isolated from the grain of a cereal crop variety prepared using the above method, and a method of preparing a thickened foodstuff comprising combining a foodstuff, water, and an effective amount of a starch isolated from the grain of a cereal crop variety prepared using the method, and cooking the resulting composition as necessary to produce a thickened foodstuff.

This invention also concerns cereal crop varieties prepared by transformation using the above method, flours prepared from the grain of said cereal crop varieties, and the preparation of breads, baked goods, and pastas by combining water, food ingredients, and an effective amount of flour from the grain of cereals crop varieties prepared using the method, and cooking the resulting composition as necessary to produce a bread, baked good, or pasta product.

BRIEF DESCRIPTION OF THE DRAWINGS

The invention can be more fully understood from the following detailed description and the accompanying drawings and the sequence descriptions which form a part of this application.

BRIEF DESCRIPTION OF THE SEQUENCES

Figure 1:
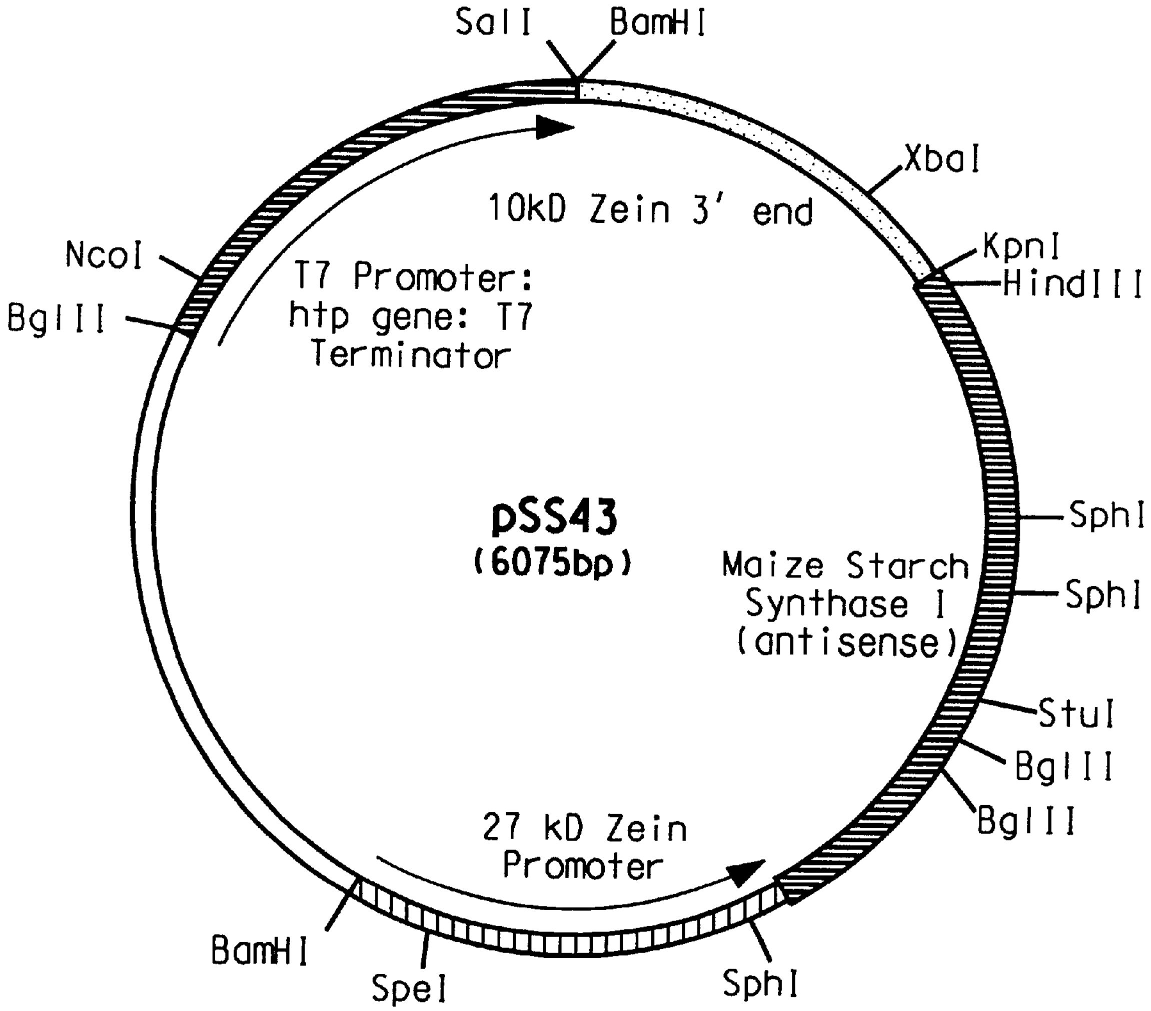
FIG. 1 presents a restriction map of plasmid pSS43.

SEQ ID NO:1 depicts the nucleotide sequence of the BE62 PCR primer.

SEQ ID NO:2 depicts the nucleotide sequence of the BE61 PCR primer.

SEQ ID NO:3 depicts the nucleotide sequence of the SS7 PCR primer.

SEQ ID NO:4 depicts the nucleotide sequence of the SS8 PCR primer.

SEQ ID NO:5 depicts the nucleotide sequence of the SS1 composite gene sequence.

SEQ ID NO:6 depicts the nucleotide sequence of the SS1 DNA sequence inserted into pSS43.

SEQ ID NO:7 depicts the nucleotide sequence of the MM50 PCR primer.

SEQ ID NO:8 depicts the nucleotide sequence of the BE56 PCR primer.

SEQ ID NO:9 depicts the nucleotide sequence of the MM62 PCR primer.

SEQ ID NO:10 depicts the nucleotide sequence of the MM60 PCR primer.

SEQ ID NO:11 depicts the nucleotide sequence of the SS1 DNA sequence inserted into pSS64-C5.

SEQ ID NO:12 depicts the nucleotide sequence of the SS1 DNA sequence in serted into pSS65-c11.

SEQ ID NO:13 depicts the nucleotide sequence of the SS9 PCR primer.

SEQ ID NO:14 depicts the nucleotide sequence of the SS10 PCR primer.

SEQ ID NO:15 depicts the nucleotide sequence of SSb insert sequence of pSPB37.

SEQ ID NO:16 depicts the nucleotide sequence of the SSb DNA sequence inserted into pSPB40.

SEQ ID NO:17 depicts the nucleotide sequence of the OSPB104 PCR primer.

SEQ ID NO:18 depicts the nucleotide sequence of the OSPB105 PCR primer.

SEQ ID NO:19 depicts the nucleotide ssequence of the OSPB106 PCR primer.

SEQ ID NO:20 depicts the nucleotide sequence of the SSb DNA sequence inserted into pSPB47.

The Sequence Descriptions contain the one letter code for nucleotide sequence characters and the three letter codes for amino acids as defined in conformity with the IUPAC-IUB standards (1985, *Nucleic Acids Res.* 13:3021–3030, and 1984, *Biochem. J* 219:345–373) which are incorporated by reference herein.

DETAILED DESCRIPTION OF THE INVENTION

In the context of this disclosure, a number of terms shall be utilized. As used herein, the term "starch" refers to a polysaccharide consisting of α-D-(1,4) glucan that may contain a variable proportion of α-D-(1,6) branches. As used herein, the term "starch fine structure" refers to the molecular structure of a starch polymer, the presence, abundance and distribution of α-D-(1,6) bonds and the presence, abundance and length of both branched and unbranched α-D-(1,4) glucans in the polymer. Starch fine structure is described by amylopectin branch chain distribution, or by the relative proportion of amylose to amylopectin, or by the degree of polymerization of amylose. Alteration of any of these structural molecular components results in an altered starch fine structure. One, two or all three of these parameters may be altered independently of one another. The term "degree of polymerization" refers to the number of α-D-glucopyranose units in a molecule or designated portion of a molecule such as a branch chain of amylopectin. As used herein, the term "branch chain distribution" refers to the distribution of α-1,4-linked glucan chains which is detected following isoamylase digestion of amylopectin and subsequent fractionation of the liberated branches by size exclusion chromatography.

As used herein "cereal crops" mean a plant yielding a seed containing starch suitable for food or industrial use, as exemplified by maize (corn), rice, sorghum, wheat and barley. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "essentially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not affect the functional properties of the resulting transcript vis-a-vis the ability to mediate alteration of gene expression by antisense or co-suppression technology or alteration of the functional properties of the resulting protein molecule. It is therefore understood that the invention encompasses more than the specific exemplary sequences. For example, it is well known in the art that antisense suppression and co-suppression of gene expression may be accomplished using nucleic acid fragments representing less than the entire coding region of a gene, and by nucleic acid fragments that do not share 100% identity with the gene to be suppressed (U.S. Pat. No. 5,107,065). Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine. Likewise, a codon for the amino acid alanine may be substituted by a codon encoding a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the DNA sequence of the nucleic acid fragments reported herein. More preferred nucleic acid fragments are 90% identical to the DNA sequence of the nucleic acid fragments reported herein. Most preferred are nucleic acid fragments that are 95% identical to the DNA sequence of the nucleic acid fragments reported herein. The percent identity used herein, can be precisely determined by the DNASTAR protein alignment protocol using the Jotun-Hein algorithm (Hein, J. J. (1990) *Meth. Enz.* 183: 626–645). Default parameters for the Jotun-Hein method for multiple alignments are: GAP PENALTY=11, GAP LENGTH PENALTY=3; for pairwise alignments KTUPLE 6.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding SS1 or SSb proteins as set forth in SEQ ID NOs:5, 11, 12, 15, 16 and 20. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochem. Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences are described in Turner, R. and Foster, G. D. (1995) *Molecular Biotechnology* 3:225.

The expression "3' non-coding sequences" refers to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to a product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to an RNA that is without introns and that can be translated into protein by the cell. "cDNA" refers to a double-stranded DNA that is complementary to and derived from mRNA. "Sense" RNA refers to an RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers a phenomenon in plants whereby foreign or endogenous genes are silenced by the introduction of sufficiently homologous transgenes. The mechanism(s) of gene inactivation are not well understood but may occur by either blocking transcription or by inhibiting mRNA accumulation. For example, U.S. Pat. No. 5,231,020 describes the production of sense RNA transcripts capable of suppressing the expression of identical or essentially similar foreign or endogenous genes.

"Altered levels" refers to the production of gene product (s) in transgenic organisms in amounts or proportions that differ from that of normal or non-transformed organisms.

"Transformation" refers to the transfer of a nucleic acid fragment into the genome of a host organism, resulting in genetically stable inheritence. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

The term "pasting" refers to an irreversible physical change in starch granules or a suspension of starch granules characterized by swelling and hydration of granules, a rapid increase in viscosity of a suspension, and the formation of a sol from the suspension. This change is also known as cooking or gelatinization. The abbreviation "SNU" refers to the stirring number unit, approximately equal to 10 centipoise, which is a measure of viscosity. For conversion to SI units (pascal seconds), multiply centipoise by 1000, i.e., 1 PaSec=1000 cp. Hence, 1 SNU=0.01 PaSec. The term "sol" refers to a fluid colloidal system. The term "viscosity" is a measure of the internal friction of a fluid that can be thought of as the consistency or thickness of a fluid.

This invention concerns the construction of transgenic grain bearing plants wherein the expression of genes encoding enzymes involved in starch synthesis, specifically starch polymer formation (starch synthases) are modulated to effect a change in the branch chain distribution of the amylopectin, the relative proportion of amylose to amylopectin, or the degree of polymerization of amylose component of starch. Such modification of starch fine structure results in alteration of the physical properties of starch isolated from the transgenic grain crops. This alteration in the starch fine structure will lead to generation of novel starches possessing properties that are beneficial in food and industrial applications.

Preferred among these genes are the genes encoding monocot starch synthase other than GBSSI, the cloning of which was discussed above. These genes can be isolated by techniques routinely employed by the skilled artisan for isolation of genes when the nucleotide sequence of the desired gene is known, or when the sequence of a homologous gene from another organism is known. Sequence information about the desired gene can be used to prepare oligonucleotide probes for identification and isolation of the entire starch synthase enzyme gene from an appropriate genetic library. This library may be a genomic library, wherein the coding region may be contained on a single DNA fragment or may be contained on several distinct DNA fragments. Moreover, two or more exons encoding the starch synthase enzyme may be separated by one or more introns. Alternatively, the library may be a cDNA library wherein the liklihood of isolating a cDNA clone comprising the entire coding region as one contiguous sequence is greater. In either instance, the appropriate clone(s) can be identified by DNA-DNA hybridization with probes corresponding to one or more portions of the desired genes. Alternatively, oligonucleotide primers can be prepared and employed as PCR primers in order to amplify and subsequently isolate all or part of the starch synthase enzyme coding region from genomic DNA, or from the genomic or cDNA libraries described above.

Several different assays can be used to measure starch synthase enzyme activity. Activity may be assayed using a variety of methods that assess the incorporation of radiolabelled ADP-Glucose ($^{14}$C-Glucose) into alcohol-insoluble polymer (Pollock and Priess (1980) *Arch. Biochem. Biphys.* 204, 578–588; Keeling et al. (1994) *Aust. J Plant Physiol.* 21:807–827; Fontaine et al. 1993 *J Biol. Chem.* 268:16223–16230). The method of Keeling et al. is typical. Endosperm tissue from developing corn kernels is dissected, lyophilized and ground in liquid nitrogen. An extract is prepared by suspending 100 mg of ground tissue in 2 ml of buffer (50 mM Hepes, pH 7.5, 5 mM $MgCl_2$, 1 mM DTT) and homogenized with a mechanical homogenizer. The homogenate is centrifuged at 30,000×g and the supernatant is assayed for soluble starch synthase activity. Briefly, soluble synthase activity is assayed in 1.5 mL tubes with 25 mL of rabbit liver glycogen (2 mg) and 100 mL of buffer (200 mM Bicine, 9 mM EDTA, 50 mM KCl and 20 mM reduced glutathione, pH 8.3). 50 mL of the soluble extract is added and pre-incubated for 2 minutes. The assay is started with the addition of 25 mL 8.0 mM ADP-Glucose ($^{14}$C, 444 dpm nmol-1) and allowed to proceed for 10 minutes before the addition of 100 mL of 0.25 M NaOH. Glucan is precipitated by addition of 1.0 mL of methanol, chilling on ice for 5 minutes, and centrifugation. The glucan is resolubilized in 0.1 M NaOH and precipitated a second time with methanol. The precipitate is then gelatinized by heating before the addition of scintillation cocktail and measurement of radioactivity in a scintillation counter.

In order to alter the starch fine structure in corn, a chimeric gene is constructed wherein expression of the gene encoding the starch synthase enzyme is under the control of regulatory elements suitable to expression of the gene 1) in desired plant tissues, 2) at stages of development that provide the maximum desired effect, and 3) at levels of gene expression that result in alteration of starch synthase enzyme function such that expression affects a measurable and significant change in starch fine structure. The expression of foreign genes in plants is well-established (Klein et al. (1987) *Nature* (London) 327:70–73, and De Blaere et al. (1987) *Meth. Enzymol.* 143:277–291). Proper level of expression of sense or antisense synthase enzyme genes in corn may require the use of different chimeric genes utilizing different regulatory elements. Moreover, effective modulation of endogenous starch synthase gene expression by cosupression or antisense supression may require construction of chimeric genes comprising different regions of the starch synthase sense or antisense sequences. The well-known variability of the cosuppression and antisense techniques indicates that even while using different genetic constructs, multiple plants may have to be screened in order to identify those with the desired phenotype.

Promoters utilized to drive gene expression in transgenic plants can be derived from many sources so long as the chosen promoter(s) have sufficient transcriptional activity to accomplish the invention by expressing translatable mRNA, mRNA suitable for cosuppression, or antisense RNA in the desired host tissue. For example, promoters for expression in a wide array of plant organs include those directing the 19S and 35S transcripts in Cauliflower mosaic virus (Odell et al. (1985) *Nature* 313:810–812; Hull et al. (1987) *Virology* 86:482–493), small subunit of ribulose 1,5-bisphosphate carboxylase (Morelli et al. (1985) *Nature* 315:200–204; Broglie et al. (1984) *Science* 224:838–843; Hererra-Estrella et al. (1984) *Nature* 310:115–120; Coruzzi et al. (1984) *EMBO J.* 3:1671–1679; Faciotti et al. (1985) *Bio/Technology* 3:241) and chlorophyll a/b binding protein (Lamppa et al. (1986) *Nature* 316:750–752).

Depending upon the application, it may be desirable to select promoters that are specific for expression in one or more organs of the plant. Examples include the light-inducible promoters of the small subunit of ribulose 1,5-bisphosphate carboxylase, if the expression is desired in photosynthetic organs, or promoters active specifically in seeds.

Preferred promoters are those that allow expression specifically in seeds. This may be especially useful, since seeds are the primary location of long-term starch accumulation. In addition, seed-specific expression may avoid any potential deleterious effects that starch synthase enzyme modulation may have on non-seed organs. Examples of seed-specific promoters include, but are not limited to, the promoters of seed storage proteins. The expression of seed storage proteins is strictly regulated in the plant, being expressed almost exclusively in seeds in a highly organ-specific and stage-specific manner (Higgins et al. (1984) *Ann. Rev. Plant Physiol.* 35:191–221; Goldberg et al. (1989) *Cell* 56:149–160; Thompson et al. (1989) *BioEssays* 10:108–113). Moreover, different seed storage proteins may be expressed at different stages of seed development. There are currently numerous examples for seed-specific expression of seed storage protein genes in transgenic plants. These include genes from monocotyledonous plants such as for barley β-hordein (Marris et al. (1988) *Plant Mol. Biol.* 10:359–366) and wheat glutenin (Colot et al. (1987) *EMBO J.* 6:3559–3564). Moreover, promoters of seed-specific genes, operably linked to heterologous coding sequences in chimeric gene constructs, also maintain their temporal and spatial expression pattern in transgenic plants (Goldberg et al. (1989) *Cell* 56:149–160). Such examples include linking either the phaseolin or *Arabidopsis* 2S albumin promoters to the Brazil nut 2S albumin coding sequence and expressing such combinations in tobacco, *Arabidopsis,* or *Brassica napus* (Altenbach et al. (1989) *Plant Mol. Biol.* 13:513–522; Altenbach et al. (1992) Plant *Mol. Biol.* 18:235–245; De Clercq et al. (1990) *Plant Physiol* 94:970–979), the use of bean lectin and bean b-phaseolin promoters to express luciferase (Riggs et al. (1989) *Plant Sci.* 63:47–57), and wheat glutenin promoters to express chloramphenicol acetyl transferase (Colot et al. (1987) *EMBO J.* 6:3559–3564).

Of particular use in the expression of the nucleic acid fragment(s) of the invention will be promoters from several extensively characterized corn seed storage protein genes such as endosperm-specific promoters from the 10 kD zein gene (Kirihara et al. (1988) *Gene* 71:359–370), the 15 kD zein gene (Hoffman et al. (1987) *EMBO J.* 6:3213–3221; Schernthaner et al. (1988) *EMBO J.* 7:1249–1253; Williamson et al. (1988) *Plant Physiol.* 88:1002–1007), the 27 kD zein gene (Prat et al. (1987) *Gene* 52:51–49; Gallardo et al. (1988) *Plant Sci.* 54:211–281), and the 19 kD zein gene (Marks et al. (1985) *J. Biol. Chem.* 260:16451–16459). The relative transcriptional activities of these promoters in corn have been reported (Kodrzyck et al. (1989) *Plant Cell* 1:105–114) providing a basis for choosing a promoter for use in chimeric gene constructs for corn. Moreover, promoters that drive the expression of genes encoding enzymes involved in starch biosythesis may be used in the practice of this invention. These include but are not limited to the 5' regulatory sequences of the sucrose synthase (Yang, N. S. and Russell, D. (1990) *Proc. Natl. Acad Sci.USA* 87:4144–4148), the waxy or granule-bound starch synthase I (Unger et al. (1991) *Plant Physiol.* 96:124) genes, the sh2 (Bhave et al. (1990) *Plant Cell* 2:581–588) and bt2 (Bae et al. (1990) *Maydica* 35:317–322) genes whose products constitute the enzyme ADP-glucose pyrophosphorylase. The skilled artisan will recognize that those earlier examples can now be supplemented by the plethora of starch biosynthetic and other seed specific genes isolated using modern genomic science techniques, which provide an almost unlimited source of seed specific promoters which can be used for the purposes of practicing the present invention. Where necessary, cDNA clones can be used to isolate genomic clones containing the regulatory sequences of intxerest. Expression from any of these promoters could be increased by the use of enhancer sequences, including those found in intron sequences (see, for examples, Callis et al. (1987) *Genes Dev.* 1:1183–1200; Maas et al. (1991) *Plant Mol. Biol.* 16:199–207; Luehrsen, K. R. and Walbot, V. (1991) *Mol. Gen. Genet.* 225:81–93; Oard et al. (1989) *Plant Cell Rep* 8:156–160).

Any 3' non-coding region capable of providing a polyadenylation signal and other regulatory sequences that may be required for proper expression can be used to accomplish the invention. This would include the 3' end from any storage protein such as the 3' end of the 10 kD, 15 kD, 27 kD and alpha zein genes, the 3' end of the bean phaseolin gene, the 3' end of the soybean β-conglycinin gene, the 3' end from viral genes such as the 3' end of the 35S or the 19S cauliflower mosaic virus transcripts, the 3' end from the opine synthesis genes, the 3' ends of genes encoding ribulose 1,5-bisphosphate carboxylase or chlorophyll a/b binding protein, or 3' end sequences from any gene such that the sequence employed provides the necessary regulatory information within its nucleic acid sequence to result in the proper expression of the promoter/coding region combination to which it is operably linked. There are numerous examples in the art that teach the usefulness of different 3' non-coding regions (for example, see Ingelbrecht et al. (1989) *Plant Cell* 1:671–680). Various methods of introducing a DNA sequence (i.e., of transforming) into eukaryotic cells of higher plants are available to those skilled in the art (see EPO publications 0 295 959 A2 and 0 138 341 A1). Such methods include high-velocity ballistic bombardment with metal particles coated with the nucleic acid constructs (see Klein et al. (1987) *Nature* (London) 327:70–73, and see U.S. Pat. No. 4,945,050), as well as those based on transformation vectors based on the Ti and Ri plasmids of Agrobacterium spp., particularly the binary type of these vectors. Ti-derived vectors transform a wide variety of higher plants, including dicotyledonous plants, such as soybean, cotton and rape (Pacciotti et al. (1985) Bio/Technology 3:241; Byrne et al. (1987) Plant Cell, Tissue and Organ Culture 8:3; Sukhapinda et al. (1987) Plant Mol. Biol. 8:209–216; Lorz et al. (1985) Mol. Gen. Genet. 199:178–182; Potrykus et al. (1985) Mol. Gen. Genet. 199:183–188); Qu, R. et al. (1996) Dev. Bio.-Plant 32:233–240; Vasil, V. et al. (1993) Bio/Technology 11:1553–1558 and more recently monocots such as rice and corn Hiei, Y. et al. (1994) *Plant J* 6:271–282.

Other transformation methods are available to those skilled in the art, such as direct uptake of foreign DNA constructs (EPO publication 0 295 959 A2), and techniques of electroporation (Fromm et al. (1986) *Nature* (London) 319:791–793). Once transformed, the cells can be regenerated into mature plants by those skilled in the art. Also relevant are several recently described methods of introducing nucleic acid fragments into commercially important crops, such as rapeseed (De Block et al. (1989) *Plant Physiol.* 91:694–701), sunflower (Everett et al. (1987) *Bio/Technology* 5:1201–1204), soybean (McCabe et al. (1988) *Bio/Technology* 6:923–926; Hinchee et al. (1988) Bio/Technology 6:915–922; Chee et al. (1989) *Plant Physiol.* 91:1212–1218; Christou et al. (1989) *Proc. Natl. Acad. Sci USA* 86:7500–7504; EPO Publication 0 301 749 A2), rice (Qu R. et al. (1996) *Dev. Bio-Plant* 32:233–240; Hie Y. et al. (1994) *Plant J.* 6:271–282), wheat (Vasel V. et al. (1993) *Bio/Technology* 11:1553–1558), and corn (Gordon-Kamm et al. (1990) *Plant Cell* 2:603–618; Fromm et al. (1990) *Bio/Technology* 8:833–839).

One skilled in the art is familiar with still other means for the production of transgenic maize plants including introduction of DNA into protoplasts and regeneration of plants from said protoplasts (Omirulleh et al. (1993) *Plant Mol. Biol.* 21:415–423), electroporation of intact tissues (D'Halluin et al. (1992) *Plant Cell* 4:1495–1505; Laursen et al. (1994) *Plant Mol. Biol.* 24:51–61), silica carbide mediated fiber transformation of maize cells (Kaeppler et al. (1992) *Theor. Appl. Genet.* 84:560–566; Frame et al. (1994) *Plant J.* 6:941–948). In addition to the method of particle bombardment of maize callus cells described above, one skilled in the art is familiar with particle bombardment of maize scutellar or suspension cultures to yield fertile transgenic plants (Koziel et al. (1993) *Bio/Technology* 11:194–200; Walters et al. (1992) *Plant Mol. Biol.* 18:189–200).

The person skilled in the art will know that special considerations are associated with the use of antisense or cosuppresion technologies in order to reduce expression of particular genes. U.S. Pat. Nos. 5,190,931, 5,107,065 and 5,283,323 disclose the feasibility of these techniques. Once transgenic plants are obtained by one of the methods described above, it will be necessary to screen individual transgenics for those that most effectively display the desired phenotype. It is well known to those skilled in the art that individual transgenic plants carrying the same construct may differ in expression levels; this phenomenon is commonly referred to as "position effect". For example, when the construct in question is designed to express higher levels of the gene of interest, individual plants will vary in the amount of the protein produced and thus in enzyme activity; this in turn will effect the phenotype. Thus, in the use of these techniques their efficiency in an individual transgenic plant is unpredictable, but given a large transgenic population individuals with suppressed gene expression will be obtained. In either case, in order to save time, the person skilled in the art will make multiple genetic constructs containing one or more different parts of the gene to be suppressed, since the art does not teach a method to predict which will be most effective for a particular gene. Furthermore, even the most effective constructs will give an effective suppression phenotype only in a fraction of the individual transgenic lines isolated. For example, WO 93/11245 and WO 94/11516 disclose that when attempting to suppress the expression of fatty acid desaturase genes in canola, actual suppression was obtained in less than 1% of the lines tested. In other species the percentage is somewhat higher, but in no case does the percentage reach 100. This should not be seen as a limitation on the present invention, but instead as practical matter that is appreciated and anticipated by the person skilled in this art. Accordingly, the skilled artisan will develop methods for screening large numbers of transformants. The nature of these screens will generally be chosen on practical grounds, and is not an inherent part of the invention. In the instant case, for example, one can screen by looking for changes in starch phenotype using chromatography to determine relative proportions of amylose to amylopectin, amylopectin branch chain distribution, degree of polymerization, Rapid Visco Analysis, a standard industry technique for measuring functionality of food hydrocolloids, particularly starches (as is done in the examples), or other means. One could equally use antibodies specific for the protein encoded by the gene being suppressed, or one could establish assays that specifically measure enzyme activity. A preferred method will be one which allows large numbers of samples to be processed rapidly, since it will be expected that the majority of samples will be negative.

Plants that are identified to have the altered starch fine structure in the grain present unique genetic material which provide advantages over traditional cereal crops lines and known starch mutants. Use of lines of the instant invention with inhibited expression of SS isoforms in cereal crop breeding provide a dominant trait that can simplify and speed the breeding process. Known starch mutants can be used but they are often recessive and present more complications. Additionally for cereal crops such as wheat, there are a limited number of mutants known. Further, the use of antisense or cosuppression to inhibit SS isoforms leads to variable levels of inhibition due to chromosomal position effects. The resulting variable levels of SS activities would lead to a wide range of phenotypes that is not possible using traditional mutants which can result in a limited dosage series of a mutant allele in cereal crops endosperm. Additional unique and potentially valuable starch fine structures will result from crossing the newly developed corn lines with altered SS activities with each other and/or known starch mutants such as wx or ae.

EXAMPLES

The present invention is further defined in the following examples. It will be understood that the examples are given for illustration only and the present invention is not limited to uses described in the examples. Temperature values are presented in degrees celcius and percent values are weight to volume, unless stated otherwise. The present invention can be used to generate transgenic cereal crops whose altered starches may be used for any purpose where its properties are usefil such as in, but not limited to, foods, paper, plastics, adhesives, or paint. From the above discussion and the following examples, one skilled in the art can ascertain, and without departing from the spirit and scope thereof, can make various changes and modifications of the invention to adapt it to various usages and conditions. All such modifications are intended to fall within the scope of the claims.

Example 1

Preparation of Transgenic Corn Expressing an Antisense Construct of Corn Starch Synthase I Isolation of Corn Starch Synthase I Clones The cDNA sequence of a soluble starch synthase from rice (Baba T. et al. (1993) *Plant Physiol.* 103:565–573) was used to generate DNA probes for the detection of homologous starch synthase sequences in corn. Oligonucleotides BE62 (SEQ ID NO:1) and BE61 (SEQ ID NO:2) were synthesized on a Beckman Oligo 1000™ Oligonucleotide Synthesizer. These primers encompass nucleotides (nt) 1600–1619 and 1826–1808 respectively of the published rice sequence.

5'-AAGCTTGAATTCCACAGAATCAGGGTACAGG-3' [SEQ ID NO:1]

5'-GAAGGACTGGCACTAGACTGG-3' [SEQ ID NO:2]

The primer pair was used to amplify a 429 bp DNA fragment from rice genomic DNA using standard PCR conditions specified in the GeneAmp® PCR kit (Perkin Elmer). Amplification was carried out for 30 cycles consisting of 1 minute at 94°, 2 minutes at 55° and 3 minutes at 72°, followed by a final 7 minute extension at 72° after the last cycle. Nucleotide sequence analysis showed that the amplified fragment (SSI) contained the expected cDNA sequence as well as a 124 bp intron following nt 1678 and an 81 bp intron following nt 1788 of the published sequence. The DNA fragment was labeled by nick translation and used to probe Northern blots of total RNA from developing corn kernels. A 2.6 kb maize transcript was detected that was present as early as 10 days after pollination (DAP) and reached a maximal level 22 DAP. The rice SS1 fragment was designed to contain 2 regions of sequence homology found to be shared by plant and bacterial starch or glycogen synthases (Baba T. et al. (1993) *Plant Physiol.* 103:565–573). A second soluble starch synthase fragment (SS2) which lacks these regions of amino acid conservation was obtained by PCR amplification of rice DNA using a primer pair encompassing nt 1083–1103 (SS7; SEQ ID NO:3) and nt 1440–1459 (SS8; SEQ ID NO:4) of the cDNA.

5'-GGATCCGAATTCTCCTTTCTCAGCAAACGG-3' [SEQ ID NO:3]

5'-AAGCTTGAATTCCTGGGATTGCCACCTGAATTG-3' [SEQ ID NO:4]

A 900 bp DNA fragment apparently containing one or several introns was obtained. When used as a hybridization probe on blots of total corn RNA, this fragment detected a similar sized transcript (2.7 kb) whose expression profile matched that observed with the SSI probe. The SS2 fragment then was used to screen a 19 DAP corn endosperrn cDNA library for sequences homologous to that of rice soluble starch synthase.

A maize cDNA library was constructed by Clontech using polyA+RNA from endosperm tissue harvested 19 DAP. cDNAs were cloned as EcoRI-XhoI inserts in the vector lambda-ZAPII (Stratagene). Approximately 120,000 plaque-forming units of the unamplified library were plated onto NZY agar plates and transferred in duplicate to nitrocellulose membranes (Sambrook, J., Fritsch, E. F., and Maniatis, T. (1989) Molecular Cloning, Cold Spring Harbor Laboratory Press, New York; hereinafter "Maniatis"). The immobilized DNA was hybridized for 16 hours at 51° to nick translated SS2 ($2\times10^5$ dpm/ml) in 6×SSPE, 5×Denhardt's 0.5% SDS, 100 mg/ml denatured salmon sperm DNA (Maniatis). Filters were washed twice in 2×SSC, 0.1% SDS at room temperature for 30 minutes each time and once in 1×SSC, 0.1% SDS for 15 minutes at 50° (Maniatis). A total of 38 putative positive plaques were identified from this initial screen. Of these, 24 were purified and subjected to further characterization by restriction enzyme digestion and partial nucleotide sequence analysis. Two clones, designated pSS23 and pSS31 contained the longest cDNA inserts and were selected for more detailed characterization. Plasmid pSS31 was found to contain a 2.2 kb cDNA insert which is comprised of 144 bp of 5' untranslated DNA, a 1923 bp open reading frame, and 168 bp of 3' untranslated DNA. Plasmid pSS31 thus encodes a complete copy of the corn starch synthase polypeptide. Comparison of the deduced amino acid sequence to that of rice soluble starch synthase shows the two proteins to be 80% identical over their entire length. pSS23 contains a 1954 bp insert whose sequence over the first 1715 nucleotides is identical to nt 521 to 2235 of pSS31. However, the cDNA insert of pSS23 extends 239 bp beyond the 3' end of pSS31. PSS23 thus contains an incomplete copy of the starch synthase polypeptide, lacking 126 amino acids at the amino terminal end. The SSI cDNA consensus sequence was obtained by comparison of the sequences of pSS23 and pSS31 and is shown in SEQ ID NO:5. Both pSS23 and pSS31 were used to generate DNA constructs for modification of the expression of this starch synthase in corn plants.

Preparation of an Expression Vector Encoding Antisense Transcripts of Corn SSI

The starch synthase clone pSS23 was used to generate an antisense construct for suppression of SSI expression in corn. pSS23 was first digested with the restriction enzyme Pvu I and the 5' recessed ends were rendered blunt by reaction with T4 DNA polymerase. To 10 mg of Pvu I-digested pSS23 (in 40 mL 10 mM Tris-HCl, pH 7.5, 100 mM NaCl, 10 mM $MgCl_2$, 1 mM DTT) 20 units of T4 DNA polymerase and deoxynucleotide triphosphates (dNTPs) were added to a final concentration of 0.1 mM. The reaction mixture was incubated for 15 minutes at 12°, 10 minutes at 75° and the DNA purified by extraction with phenol:chloroform:isoamyl alcohol (25:24:1) followed by ethanol precipitation. The repaired plasmid DNA was next incubated with the restriction enzyme Xho I in the buffer specified above. Following digestion, dNTPs were added to a final concentration of 50 $\mu$M and the Xho I ends were filled-in by reaction with the Klenow fragment of *E. coli* DNA polymerase I (10 units) and dNTPs for 15 minutes at room temperature. The enzyme was inactivated by incubation at 75° for 10 minutes and the blunt-ended DNA was fractionated by electrophoresis on a 0.7% low melting point agarose gel in 40 mM Tris-acetate, pH 8.5, 1 mM EDTA. The 1.55 kb band (insert) was excised from the gel and combined with a 4.9 kb fragment from the plasmid pML103 (ATCC 97366). Plasmid pML103 contains a 1.05 kb Sal I-Nco I promoter fragment of the maize 27 kD zein gene and a 0.96 kb Sma I-Sal I 3' fragment of the maize 10 kD zein gene in a pGem9Zf(+) vector (Promega). Plasmid pML103 was digested with Nco I and Sma I, the digested DNA was treated with Klenow and dNTPs to fill-in the overhangs left by the enzyme, and the desired 4.9 kb vector fragment was electrophored and isolated as described. The combined insert and vector fragments were melted at 68° and ligated overnight, essentially as described (Maniatis). The ligated DNA was used to transform *E. coli* XL 1-Blue cells (Epicurean Coli XL-1 Blue™; Stratagene). Bacterial transformants were screened for the presence of and the orientation of insert DNA by digestion with the restriction enzyme HindIII. The plasmid pSS42 was identified from this analysis. PSS42 contains the 1.55 kb segment of pSS23 (SEQ ID NO:6) in antisense orientation with respect to the 27 kD zein promoter fragment and the 10 kD zein 3' end. To generate a construct for plant transformation, the chimeric gene of pSS42 was released by digestion with BamHI and the 3.6 kb fragment was cloned into the BamHI site of the vector pKS17. Plasmid pKS17 contains the hygromycin B phosphotransferase (HPT) gene which confers resistance to the antibiotic hygromycin. To generate a construct for plant transformation, the chimeric gene of pSS42 was cloned into the vector pKS17. A derivative of vector pSP72 (Promega), pKS17 contains the hygromycin B phosphotransferase (HPT) gene which confers resistance to the antibiotic hygromycin. pKS17 was assembled by the addition of a T7-promoter-HPT-T7 terminator gene to a modified pSP72 plasmid from which the β-lactamase gene had been deleted. The chimeric gene of pSS42 was released by digestion with BamHI and the 3.6 kb fragment was cloned into the BamHI site of the vector pKS17. The resultant plasmid containing the 27kD zein promoter-antisense SSI-10 kD zein 3' end in pKS17 is termed pSS43 (FIG. 1).

Transformation of Corn With the SSI Antisense Construct

Immature corn embryos were dissected from developing caryopses derived from self pollinations of the "Hi-II" maize germplasm, which was selected from the F2 of maize inbreds A188×B73 (Armstrong et al.(1991), *Maize Genetics Cooperation Newsletter* 65:92–93). Hi-II germplasm has been widely used for transformation because it is characterized by a high frequency of formation of "Type II" callus. This callus is derived from the scutella of excised immature zygotic embryos in vitro. Type-II callus is especially amenable to transformation because it is friable, rapidly proliferating and highly embryogenic. The embryos were isolated 10 to 12 days after pollination when they were 1.0 to 1.5 mm long. The embryos were placed with the axis-side facing down and in contact with an agarose-solidified MS medium (Murashige, T. and Skoog, F., (1962) *Physiol. Plant.* 15:473) supplemented with 1 mg/L 2,4-D. The embryos were kept in the dark at 27°. Friable embryogenic callus consisting of undifferentiated masses of cells with somatic proembryoids and embryoids borne on suspensor structures proliferates from the scutellum of these immature embryos. The embryogenic callus isolated from the primary explant was cultured on an agarose-solidified N6 medium (Chu et al. (1975), *Sci. Sin. Peking* 18:659–668) supplemented with 1 mg/L 2,4-D, and sub-cultured on this medium every 2 to 3 weeks.

A segment of the plasmid pML108 was used in order to provide for a selectable marker in transformation experiments. This plasmid contains the bar gene (Thompson et al. (1987) *EMBO J.* 6:2519–2523), which encodes phosphinothricin acetyl transferase (PAT). The enzyme PAT confers resistance to herbicidal glutamine synthetase inhibitors such as phosphinothricin. The bar gene in pML108 is under the control of the 35S promoter from Cauliflower Mosaic Virus (Odell et al. (1985) *Nature* 313:810–812), and contains the 3' region of the octopine synthase gene from the T-DNA of the Ti plasmid of *Agrobacterium tumefaciens.* A 2116 bp HindIII fragment containing the chimeric 35S-bar-OCS gene was isolated from pML108 and was used in conjunction with trait DNA in plant trnasformation experiments.

The particle bombardment method (Klein et al. (1987) *Nature* 327:70–73) was used to transfer genes to the callus culture cells. Gold particles (1 μm in diameter) were coated with DNA using the following technique. Plasmid DNAs (1 μg of pML 108 fragment and 12 μg of pSS43) were added to 50 μl of a suspension of gold particles (60 mg per ml). Calcium chloride (50 μl of a 2.5 M solution) and spermidine free base (20 μl of a 1.0 M solution) were added to the particles. The suspension was vortexed during the addition of these solutions and for 5 minutes after addition of the last solution. After another 5 minutes, the tubes were briefly centrifuged (5 sec at 15,000 rpm) and the supernatant removed. The particles were resuspended in 140 μl of absolute ethanol, centrifuged again and the supernatant removed. The ethanol rinse was performed again and the particles resuspended in a final volume of 55 μl of ethanol. An aliquot (6 μl) of the DNA-coated gold particles was placed in the center of a Kapton™ flying disc (Bio-Rad Labs). The particles were accelerated into the corn tissue with a Biolistic™ PDS-1000/He (Bio-Rad Instruments, Hercules Calif.), using a helium pressure of 1100 psi, a gap distance of 0.5 cm and a flying distance of 1.0 cm.

For bombardment, the embryogenic tissue was placed on filter paper over agarose-solidified N6 medium supplemented with 1 mg/L 2,4-D. The tissue was arranged as a thin lawn and covered a circular area of about 5 cm in diameter. The petri dish containing the tissue was placed in the chamber of the PDS-1000/He approximately 8 cm from the stopping screen. The air in the chamber was then evacuated to a vacuum of 28 inches of Hg. The macrocarrier was accelerated with a helium shock wave using a rupture membrane that bursts when the He pressure in the shock tube reaches 1100 psi.

Four days after bombardment the tissue was transferred to N6 medium supplemented with 1 mg/L 2,4-D plus bialaphos (2–10 mg per liter), and without casein or proline (selective medium). The tissue continued to grow slowly on this medium. After one week, the tissue was again transferred to fresh N6 selective medium containing 2,4-D and bialaphos. After 6–8 weeks on the selective medium, areas of about 1 cm in diameter of actively growing callus were identified on some of the plates containing the bialaphos-supplemented medium. These calli continued to grow when sub-cultured on the selective medium. Calli which continued to grow vigorously on the selective medium were sampled for PCR analysis by freezing a callus mass of approximately 200–500 mg of fresh weight.

DNA was extracted from the collected samples by suspending frozen, ground tissue in a buffer consisting of 50 mM Tris-HCl, pH 8.0, 7M urea, 0.35 M NaCl, 20 mM EDTA, 1% n-lauryl sarkosine and incubating at 37° C. for 15 minutes. After this time, samples were extracted with a mixture of phenol-chloroform-isoamyl alcohol (25:24:1) and concentrated by precipitation with isopropanol. DNA was resuspended in 10 mM Tris-HCl, pH 8.0, 0.1 mM EDTA (100 μl) and used as the template in PCR using primers MM50 (SEQ ID NO:7) and BE56 (SEQ ID NO:8).

5'-AAGCTTGAATTCGGCACATCGGGCCTTATGG-3' [SEQ ID NO:7]

5'-GTCTAGTGCCAGTCCTTC-3' [SEQ ID NO:8]

DNA (2 μl) was combined with 20 μM of each of the primers MM50 and BE56 in a standard mixture provided by the GeneAmp® PCR kit (Perkin Elmer). Amplification was carried out for 30 cycles consisting of 1 minute at 95°, 2 minutes at 55° and 3 minutes at 72°. Samples were scored for the presence of a 546 bp target band which spans the 3' portion of the SSI fragment and the 10 kD zein 3' end. Trait gene-positive callus samples were carried forward in the transformation regimen.

Plants were regenerated from the transgenic calli by first transferring clusters of tissue to MS medium without bialaphos or 2,4-D and placed in the dark. After two weeks the tissue was transferred to regeneration medium (Fromm et al. (1990) *Bio/Technology* 8:833–839) in the light. A total of 35 corn plants were regenerated from a single transformation experiment using the pSS43 construct.

Example 2

Preparation of Transgenic Corn Expressing Sense Constructs of Corn Starch Synthase I Plasmids pSS64-C5 and pSS65-C11 encode sense transcripts of the SSI gene. For both constructs, an Nco I site was introduced at the start methionine of the SSI cDNA by PCR. Oligonucleotides MM62 (SEQ ID NO:9) and MM60 (SEQ ID NO:10) were combined with the template DNA pSS31 in a modified PCR mix (Advantage-GC™; Clontech) designed to facilitate amplification through GC-rich regions of the template DNA.

5'-GAGTCACACGCGATGGC-3' [SEQ ID NO:9]

5'-CTCTCCGCCATGGCGACGCCCTCGGCC-3' [SEQ ID NO:10]

Figure 2:
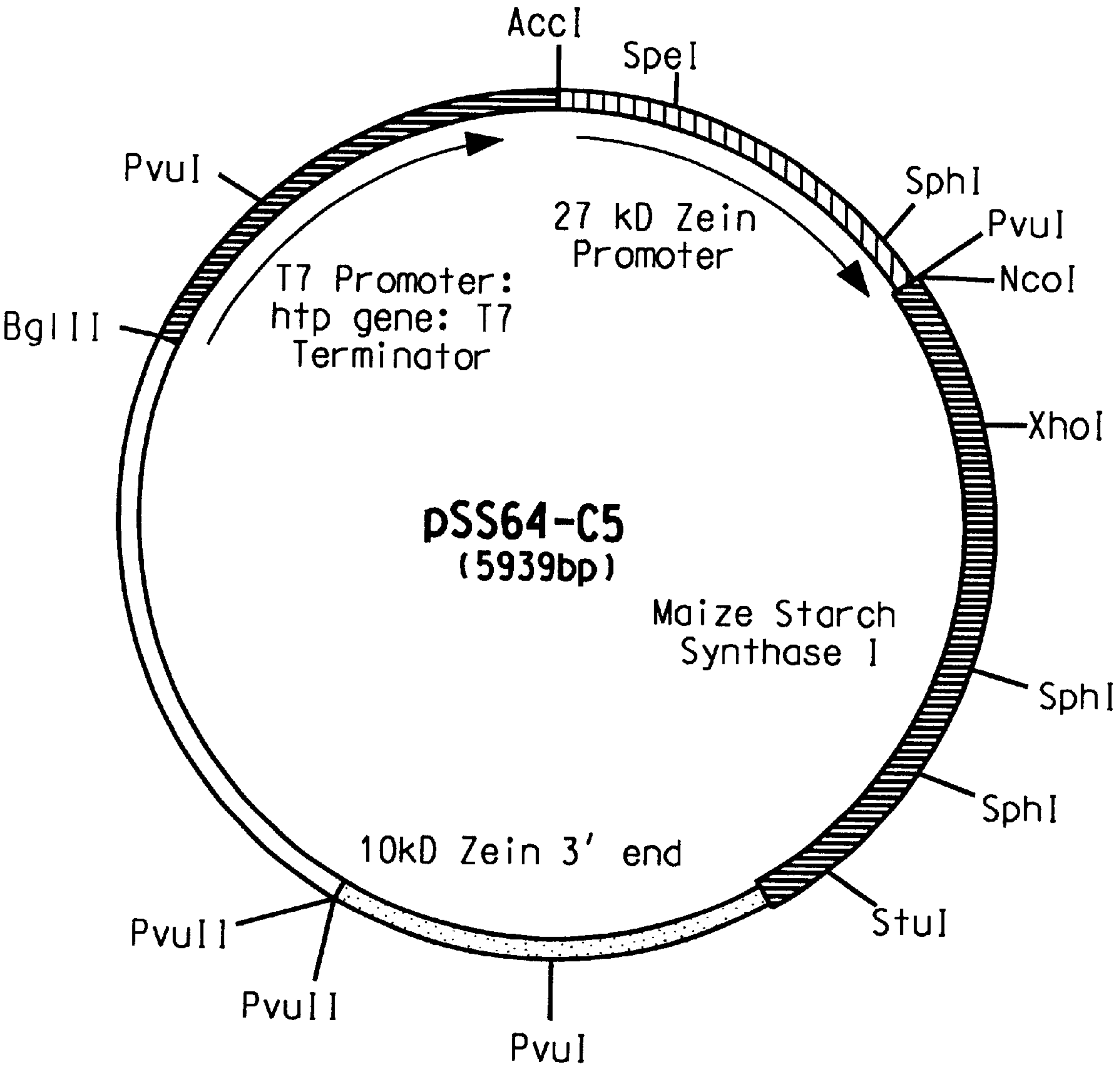
FIG. 2 presents a restriction map of plasmid pSS64-C5.
Figure 3:
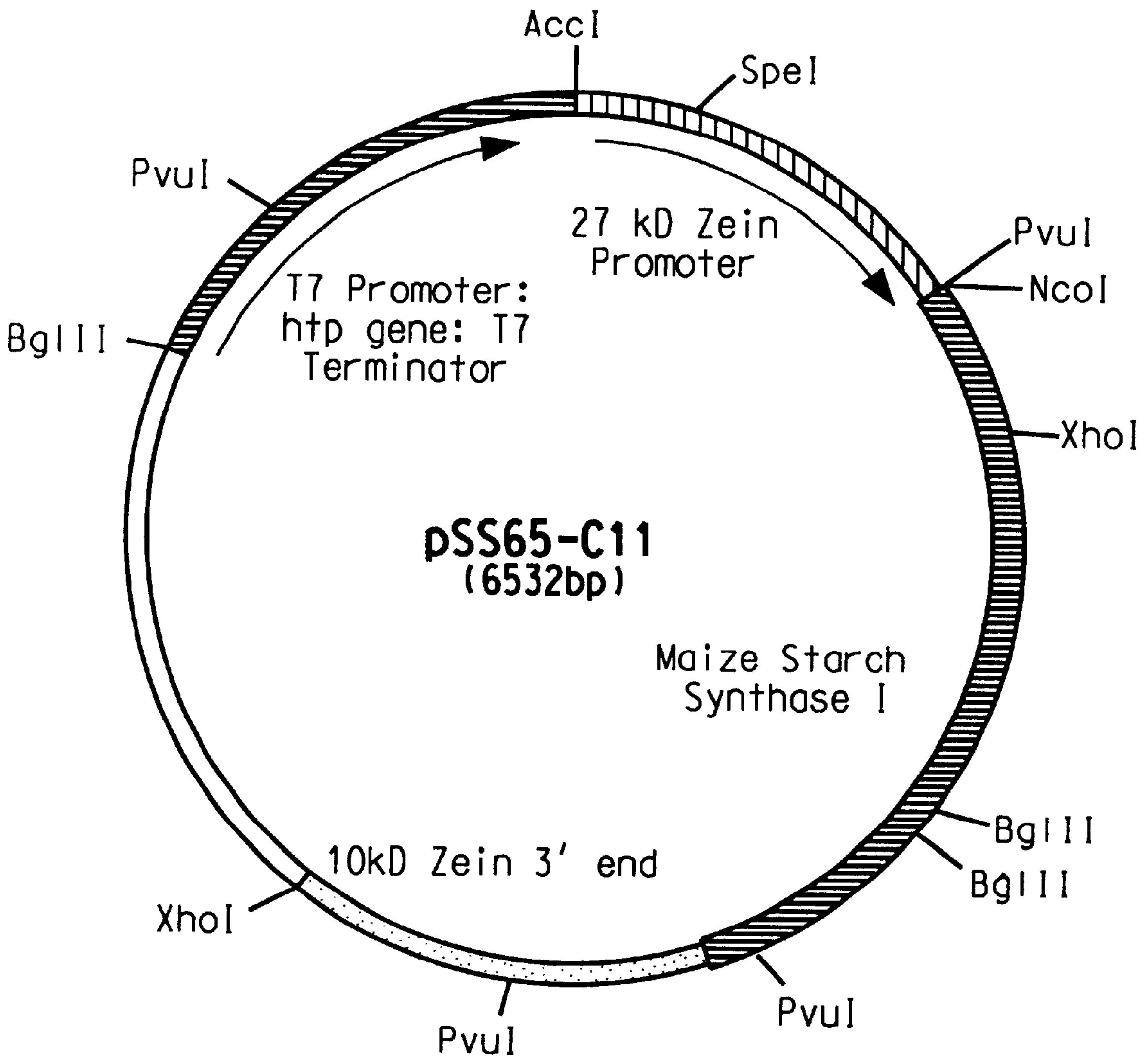
FIG. 3 presents a restriction map of plasmid pSS65-C11.

Amplification was carried out using 35 cycles of 1 minute at 95°, 1 minute at 53° and 1 minute at 72°, followed by a final 10 minute extension at 72°. The amplified fragment covers nucleotides 136–1003 of the SSI cDNA. The DNA was digested sequentially with the restriction enzymes Kpn I and Nco I, fractionated by electrophoresis on a 1% agarose gel (Maniatis) and the 537 bp Nco I-Kpn I fragment was excised from the gel and purified by treatment with Gelase™ (Epicentre Technologies). Plasmid pET-SSSI (PpuMI) contains a fragment encompassing nucleotides 418–2235 of the SSI cDNA inserted into a blunted Nco I site of pET24d (Novagen), oriented in the sense direction, and in frame with respect to the T7 promoter. The Nco I site at the 5' end of the SSI sequence was recreated upon insertion of the SSI fragment. PET-SSSI (PpuMI) was incubated with Kpn I followed by Nco I and the digest was fractionated on a 1% agarose gel. The 7.1 kb band was excised, purified and ligated to the 537 bp Nco I-Kpn I SSI fragment described above. The resultant plasmid, which contains the full coding region of SSI in addition to 168 bp of 3' untranslated DNA, is termed pET-SSSI@MAT. This plasmid was used in the construction of both pSS64-C5 and pSS65-C11. To generate pSS64-C5, PET-SSSI@MAT was digested with Bgl II and the 5' protruding ends were filled-in by reaction with Klenow and dNTPs, essentially as described above. The DNA was digested with Nco I and the released 1.485 kb fragment cloned into the 4.53 kb Nco I-Sma I fragment of pSPB38. This pSPB38 segment contains a 1.05 kb Sal I-Nco I promoter fragment of the 27 kD zein gene and a 0.96 kb Sma I-Pvu II fragment from the 3' end of the 10 kD zein gene in the vector pKS17, described above. The resultant plasmid, termed pSS64-C5 (FIG. 2), thus contains the 27 kD zein promoter followed by amino acids 1–494 of the SSI coding region (SEQ ID NO:11) and the 10 kD zein 3' end. To generate pSS65-C11, the plasmid pET-SSSI@MAT was digested with BsrGI and the 5' protruding ends were filled in by reaction with Klenow and dNTPs. The DNA was digested with Nco I to release a 2.0 kb fragment which was then ligated to the 4.53 kb pSPB38 fragment described above. The derived plasmid, pSS65-C11 (FIG. 3), consists of the entire SSI coding region followed by 84 bp from the SSI 3' untranslated DNA (SEQ ID NO:12) surrounded by the 27 kD zein promoter and the 0.96 kb 10 kD zein 3' end fragment. The DNA constructs, pSS64-C5 and pSS65-C11 were introduced into corn by the method outlined in Example 1. Trait-positive callus lines were identified by PCR analysis (Example 1) and carried forward to regenerate transgenic plants.

Example 3

Analysis of Starch from Transformed Corn Plants Containing the PSS43 Antisense Concstruct Starch was extracted from single seeds obtained from corn plants transformed with the pSS43 antisense construct. Seeds were steeped in a solution containing 1.0% lactic acid and 0.3% sodium metabisulfite, pH 3.82 and held at 52° for 22–24 h. Seeds were drained, rinsed and homogenized individually in 8–9 mL of a 100 mM NaCl solution. Five mL of toluene were added to each tube, the tubes were vigorously shaken twice for 6 minutes and were then allowed to settle for 30 minutes. Two mL of 100 mM NaCl was sprayed onto the solution, which was allowed to settle for 30 minutes, and the protein/toluene layer was aspirated off. The toluene wash step was repeated. Twelve mL water were added and shaken in a paint shaker for 45 seconds. This solution was centrifuged for 10 minutes in a table-top centrifuge and the water was removed. The water wash was repeated, followed by a final wash with 12 mL of acetone. After shaking and centrifugation steps, the acetone was drained and allowed to evaporate for 1 h. To drive off any remaining acetone starch extracts were incubated overnight in a 40° oven.

Extracted starches were enzymatically debranched as follows. Seven mg of each starch sample were added to a screw cap test tube with 1.1 mL of water. The tubes were heated to 120° for 30 minutes and then placed in a water bath at 45°. Debranching solution was made by diluting 50 μL of isoamlyase ($5\times10^6$ units/mL, Sigma) per mL of sodium acetate buffer (50 mM, pH 4.5). Forty μL of debranching solution was added to each starch sample and incubated for 3 h at 45°. Reactions were stopped by heating to 110° for 5 minutes. Debranched starch samples were lyophilized and redisolved in DMSO for analysis by gel permeation chromatography (GPC). Ten μL of debranched starch was injected and run through 3 narrow-bore columns (Polymer Labs, Mini-Mix C) in series at 100° and eluted with DMSO at a flow rate of 0.35 mL/min. Sampling interval was 30 minutes. A refractive index detector (Waters) was used with a computer running Waters Millenium Chromatography Manager System with GPC option (version 2.15.1, Waters Corp.) for detection, data collection and analysis, respectively. Retention times of pullulan standards (Standard 1: 380 kD, 100 kD, 23.7 kD, 5.8 kD, 666 and 180 mw, Standard 2: 853 kD, 186 kD, 48 kD, and 12.2 kD) were used to establish a linear calibration and calculate molecular weight distributions within the Millenium® software.

Figure 6:
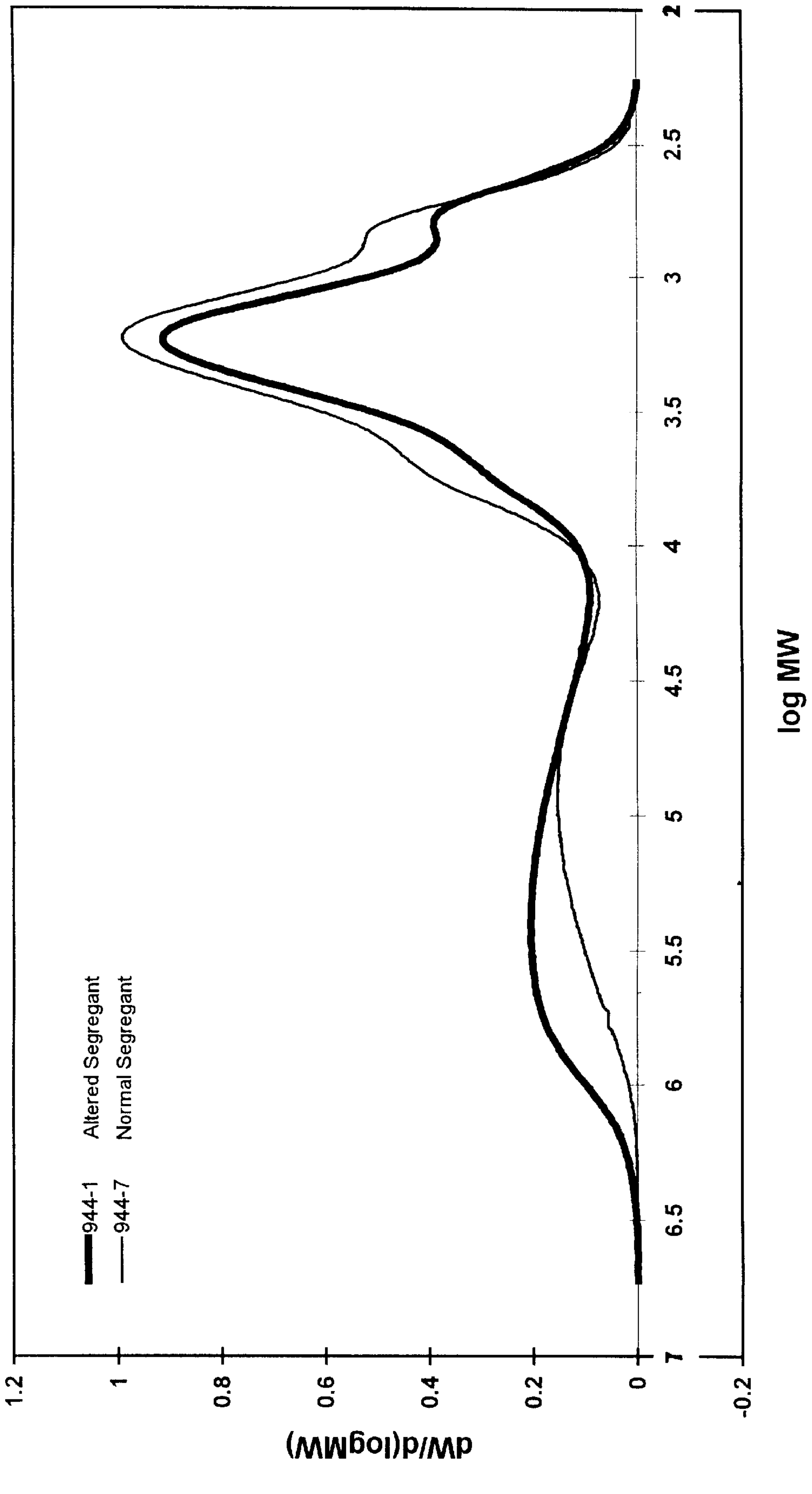
FIG. 6 presents the molecular weight distributions of debranched starch from R1 kernels of corn plants altered segregant 944-1 and normal segregant 944-7.

As known to those skilled in the art, the antisense phenomenon is generally not observed in every individual transgenic line. Therefore, individual kernels from multiple lines were examined and as expected, some, but not all lines possessed kernels demonstrating an altered starch phenotype relative to the control. As is also known to those skilled in the art transgenic corn plants produced by particle bombardment are typically heterozygous for the introduced transgene and the transgene will segregate in a predictable Mendelian fashion. On the selfed ear of a R0 (primary transformant) plant the triploid endosperm, which is the tissue responsible for starch production, will segregate 1:1:1:1 for 0, 1, 2, and 3 copies of the introduced transgene, respectively. In order to have a reasonable probability of observing any of these transgene dosages, 10 single kernels from line S048.6.1.10, (designated XBG00944-1 through XBG00944-10) were extracted for starch, and the starch from each kernel was debranched and separated as described above. FIG. 6 shows the molecular weight distributions obtained for the debranched starches from two representative kernels of line S048.6.1.10. XGB00944-7 depicts the pattern corresponding to a normal segregant while XGB00944-1 depicts the pattern corresponding to an altered segregant.

Line S048.6.1.10 produces starches with two very different types of molecular weight distributions. The molecular weight distributions of debranched starch from seeds 944-3, 944-4, 944-5, and 944-7 is typical of the molecular weight distribution observed for normal dent corn starch. The molecular weight distributions of debranched starch from seeds 944-1, 944-2, 944-6, 944-8, 944-9, and 944-10 display an alteration in the molecular weight distribution of the debranched starch. FIG. 6 depicts the molecular weight distribution of one of each of these types of seeds, 944-7 is shown as an example of a normal starch and 944-1 is an shown as an example of an altered starch. As can be seen in FIG. 6 there is an increase in the amount of high molecular weight material (log MW>4) and a decrease in the distribution of the material of lower molecular weight. The ratio of occurrence of altered and normal seeds on the segregating ear was compared to the various possible expected inheritance modes using the Chi-square ($\chi^2$) statistic. The observed frequency of 60% altered: 40% normal seeds was a reasonable fit with the simple dominance hypothesis (that either 1 or more doses of the transgene were sufficient to produce altered starch structure) ($\chi^2$=1.2) or the hypothesis that 2 or more doses of the transgene were required to alter starch structure (semidominance, $\chi^2$=0.4).

Example 4

Quantitative Analysis of Starch Structural Alterations in XBG00944 Seeds

For quantitative comparison of the altered transgenic starch the XBG00944-1 starch was chosen as a representative of the most extreme alteration in starch structure (See FIG. 6) and used for comparison to dent corn starch, starch from a dull mutant and starch from a waxy mutant. The starches from these four lines (dent, du, wx, 944-1) were enzymatically debranched as described above and separated with a slightly modified chromatography method to provide better resolution of branch chain distribution in the amylopectin fraction. Ten $\mu$L of debranched starch was injected and run through 3 narrow-bore columns (Polymer Labs, Mini-Mix C, D, E with a Mini-mix C guard column) in series at 90° and eluted with DMSO at a flow rate of 0.35 mL/min. Sampling interval was 35 minutes. A refractive index detector (Waters) was used with a computer running Waters Millenium Chromatography Manager System with GPC option (version 2.15.1, Waters Corp.) for detection and data collection and analysis, respectively. Retention times of pullulan standards (Standard 1: 380 kD, 100 kD, 23.7 kD, 5.8 kD, 666 and 180 mw, Standard 2: 853 kD, 186 kD, 48 kD, and 12.2 kD) were used to establish a 3$^{rd}$ order calibration and calculate molecular weight distributions within the Millenium® software. Three replicate analyses were performed for each of the four starches being compared.

For determination of amylose (Am) and amylopectin (Ap) content the areas under the appropriate chromatographic peaks were compared. The waxy mutant (which lacks amylose) was used to establish the appropriate molecular weight ranges for comparison. Table 1 shows the amylose and amylopectin content of each of the four lines.

TABLE 1

Amylose and Amylopectin Contents (Average (n = 3) and Standard Error Of Mean) of SSSI Antisense Starch Compared to du, dent, and wx Starches

| | % Am | Std Error | % Ap | Std Error |
|---|---|---|---|---|
| 944-1 | 35.40% | 0.15% | 64.60% | 0.15% |
| du | 31.99% | 0.05% | 68.01% | 0.05% |
| dent | 25.65% | 0.14% | 74.35% | 0.14% |
| wx | 0.00% | 0.00% | 100.00% | 0.00% |

Amylose content is significantly increased (P<0.01) compared to both normal dent starch and starch from the dull mutant. Amylopectin content is similarly significant decreased (P<0.01) compared to both lines. Suppression of starch synthase I expression has thus resulted in the alteration of starch fine structure in these plants, specifically a significant change in the ratio of amylose to amylopectin.

The Millenium® GPC software was used to produce independent molecular weight distributions of the amylose and amylopectin components of the analyzed starches and to determine molecular weight averages $M_n$ (number average molecular weight), $M_w$ (weight average molecular weight), $M_z$, and $M_{z+1}$ (sedimentation molecular weight of the polymer), peak molecular weight (MP) and polydispersity ($M_w/M_n$) for the amylose and amylopectin components.

Table 2 shows the quantitative analysis of the molecular weight distributions of amylose from 944-1, dent, and dull starch.

TABLE 2

Molecular Weight Averages (Dalton) of Amylose Component From 944-1, du, and dent Starches.

| | $M_n$ (Number Average Molecular Weight) | MP (Peak Molecular Weight) | $M_w$ (Weight Average Molecular Weight) | $M_z$ (Sedimentation Molecular Weight$_z$) | $M_{z+1}$ (Sedimentation Molecular Weight$_{z+1}$) | PD (Polydispersity, $M_w/M_n$) |
|---|---|---|---|---|---|---|
| 944-1 | 91414 ± 110 | 278047 ± 0.00 | 357427 ± 278 | 1123204 ± 12306 | 2258755 ± 48432 | 3.9100 ± 0.0074 |
| du | 82728 ± 693 | 183963 ± 13228 | 283207 ± 2727 | 894430 ± 21341 | 1908812 ± 91646 | 3.4236 ± 0.0349 |
| dent | 90511 ± 1106 | 172334 ± 8444 | 304715 ± 3480 | 968529 ± 36715 | 2095380 ± 176856 | 3.3667 ± 0.0037 |

By comparing the values under the $M_w$ column in Table 2 it can be seen that the largest amylose molecules in starch from 944-1 are significantly increased (P<0.01) in molecular weight relative to dull and dent starch. This is mirrored in significant increases in MP, $M_z$ and $M_{z+1}$. The significantly increased polydispersity (P<0.01) of the 944-1 amylose relative to both dent and dull starch suggests that this increase in the molecular weight of amylose comes not at the expense of shorter amylose molecules but rather by a broadening of the distribution of the amylose component. This is consistent with the observation of increased relative amylose content reported in Table 1, and the increased amylose content of the 944-1 line can be attributed to the occurrence of high molecular weight amylose that is not present in the dent or dull starches. The net effect, therefore, is that altering of starch synthase I expression has resulted in the alteration of starch fine structure in the seeds of these plants not only by making a significant change in the ratio of amylose to amylopectin but, because the additional amylose is larger in size, by altering the molecular weight distribution of the amylose component of the starch.

Table 3 shows the quantitative analysis of the molecular weight distributions of amylose from 944-1, dent, and dull starch.

TABLE 3

The Molecular Weight Averages (Dalton) Obtained for the Amylopectin Component of 944-1 and Control Starches

| | $M_n$ Number Average Molecular Weight) | MP (Peak Molecular Weight) | $M_w$ (Weight Average Molecular Weight) | $M_z$ (Sedimentation Molecular $Weight_z$) | $M_{z+1}$ (Sedimentation Molecular $Weight_{z+1}$) | PD (Polydispersity, $M_w/M_n$) |
|---|---|---|---|---|---|---|
| 944-1 | 2727 ± 4.5 | 2409 ± 8.3 | 3534 ± 5.8 | 4803 ± 13.9 | 6406 ± 26.9 | 1.296 ± 0.0019 |
| du | 2713 ± 6.7 | 2320 ± 8.0 | 3557 ± 11.2 | 4878 ± 20.2 | 6529 ± 35.4 | 1.311 ± 0.0009 |
| dent | 2717 ± 2.3 | 2352 ± 14.1 | 3739 ± 0.9 | 5311 ± 7.1 | 7133 ± 18.3 | 1.376 ± 0.0012 |
| wx | 2873 ± 13.0 | 2460 ± 8.7 | 4144 ± 8.6 | 6196 ± 20.3 | 8716 ± 65.8 | 1.442 ± 0.0043 |

The $M_w$ of 944-1 amylopectin is significantly reduced (P<0.01) compared to dent as are $M_z$ and $M_{z+1}$, indicative of a shift in the amylopectin chain length distribution to shorter chain lengths. The polydispersity of the 944-1 amylopectin is also significantly reduced (P<0.01) compared to dent amylopectin, as is dull, again confirming the visual observation in FIG. 6 that the amylopectin fraction of 944-1 starch is more homogeneous in chain length than is dent amylopectin.

Thus, quantitative analysis confirms a significant increase in the amylose content and an increase in the molecular weight of the amylose component of 944-1 starch compared to dent starch. The observed increase in amylose molecular weight is achieved by a broadening of the molecular weight distribution of amylose chains. The observed decrease in the amylopectin content of 944-1 starch is accompanied by a shift in the branch chain distribution to favor shorter chains.

In summary, quantitative analysis confirms that altering starch synthase I expression in corn seeds results in multiple changes in the fine structure of the starch from those seeds, including a significant increase in the amylose content, an increase in the molecular weight of the amylose component of the starch, and a shift to shorter chains in the reduced amylopectin component. The observed increase in amylose molecular weight is achieved by a broadening of the molecular weight distribution of amylose chains.

Example 5

Functional Analysis of Starach from Lines Homozygous for the 3' Antisense Construct As is known to those skilled in the art, a homozygous line can be derived from the segregating progeny of a heterozygous plant such as line S048.6.1.10 by planting a sufficient number of kernels from the segregating population, self pollinating the plants resulting from these seed, and screening single progeny seed produced to identify an ear which has fixed the altered starch trait. Once such a homozygous ear is identified, a larger sample of starch can be extracted from dry mature kernels of the identified line and control lines which produce normal dent corn starch. For each line, 15 g of kernels can be weighed into a 50 mL Erlenmeyer flask and steeped in 50 mL of steep solution (Example 3) for 18 h at 52°. The kernels are then drained and rinsed with water. The kernels are homogenized using a 20 mm Polytron probe (Kinematica GmbH; Kriens-Luzern, Switzerland) in 50 mL of cold 50 mM NaCl. The homogenate is filtered through a 72 micron mesh screen. The filtrate is brought up to a total volume of 400 mL with 50 mM NaCl and an equal volume of toluene is added. The mixture is then stirred with a magnetic stir bar for 1 h at sufficient speed to completely a emulsify the two phases. The emulsion is allowed to separate overnight in a covered beaker. The upper toluene layer is aspirated from the beaker and discarded. The starch slurry remaining in the bottom of the beaker is resuspended, poured into a 250 mL centrifuge bottle and centrifuged 15 minutes at 25,000 RCF. The supernatant is discarded and the starch is washed sequentially with water and acetone by shaking and centrifuging as above. After the acetone wash and centrifugation the acetone is decanted and the starch allowed to dry overnight in a fume hood at room temperature. A Rapid Visco Analyzer (Newport Scientific; Sydney, Australia) with high sensitivity option and Thermocline® software can be used for pasting curve analysis. For each line, 1.50 g of starch is weighed into the sample cup and 25 mL of phosphate/citrate buffer (pH 6.50) containing 1% NaCl is added. Pasting curve analysis is performed using the following temperature profile: Idle temperature 50°, hold at 50° for 0.5 minutes, linear heating to 95° for 2.5 minutes, linear cooling to 50° over 4 minutes, hold at 50° for four minutes.

Example 6

Preparation of Transgenic Corn Expressing Antisense and Sense Constructs of Corn Starch synthase SSb From the nucleotide sequence of a maize Expressed Sequence Tag (EST) with homology to starch synthases (T14684), oligonucleotides SS9 (SEQ ID NO:13) and SS10 (SEQ ID NO:14) were designed and used to amplify a 351 bp DNA fragment by PCR using standard conditions specified in the GeneAmp®PCR kit (Perkin Elmer).

5'-AAGCTTGAATTCGCAGTATGCTCGCTCTGTGC-3' [SEQ ID NO:13]

5'-GGATCCGAATTCGGTTCCACTCGCTCATGTCG-3' [SEQ ID NO:14]

Figure 4:
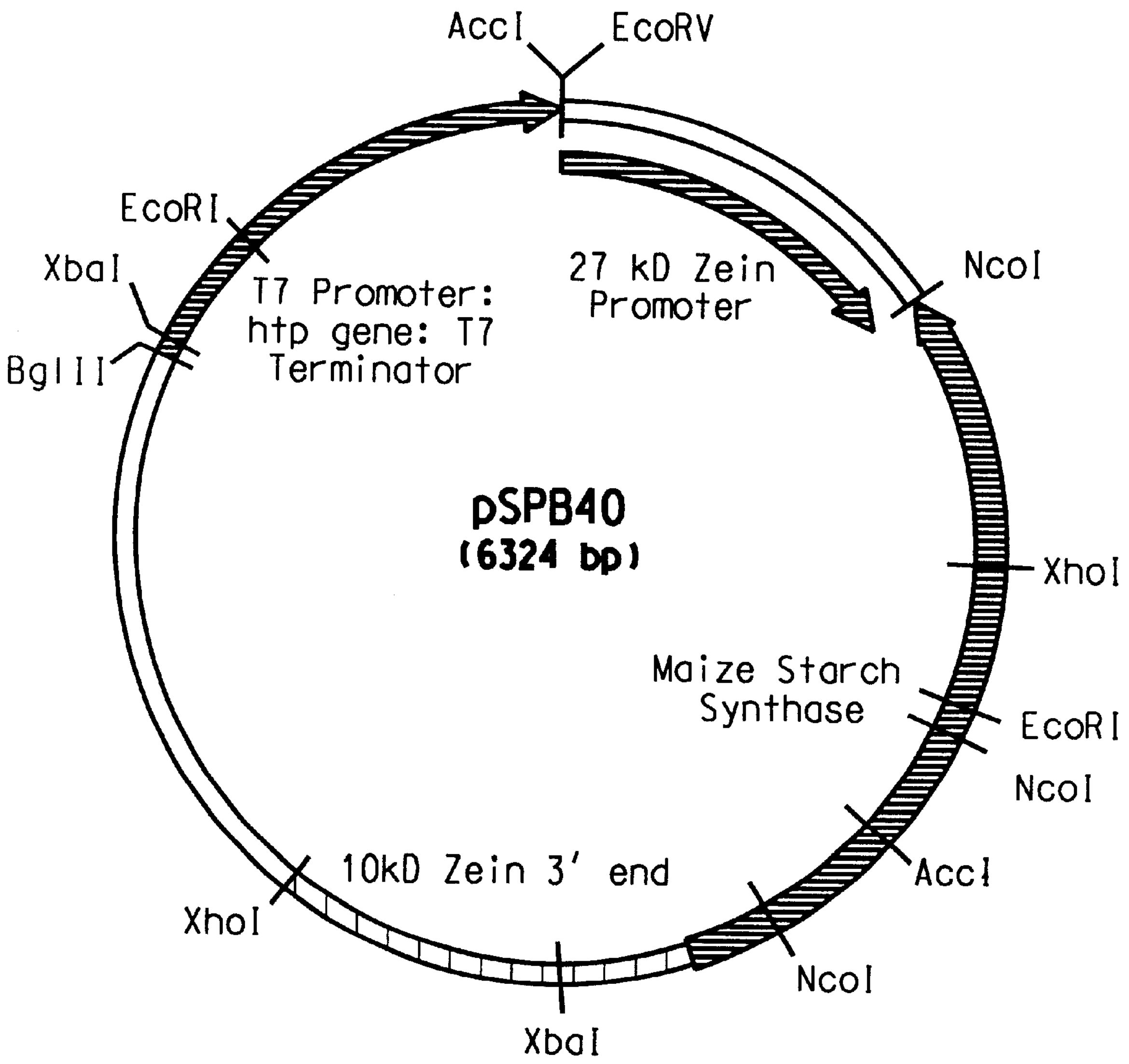
FIG. 4 presents a restriction map of plasmid pSPB40.

The resulting DNA fragment was labeled using a RadPrime DNA Labeling System (BRL Life Technologies) and then used to screen a 19 DAP corn endosperm cDNA library in lambda-ZAPII. Approximately 500,000 plaque-forming units were plated onto NZY agar plates and transferred in duplicate to nitrocellulose membranes (Maniatis). The immobilized DNA was hybridized to the labeled fragment and excess probe was removed from the filters essentially as described in Maniatis. A total of 10 positive plaques were identified, purified, and the DNA inserts subjected to further characterization. DNA sequence analysis showed that 9 of the 10 clones were related to each other and were 84% homologous over 50 bp to the probe sequence used to initially detect them. The remaining clone was distinct from the rest and showed 95% homology to T14684. Of the set of 9 clones, one, pSPB37 contained a 2006 bp insert (SEQ ID NO:15) and was used in the generation of an antisense construct for introduction into corn. The presence of an extra T in the sequence of the DNA insert of pSPB37 was first corrected by substitution of a 431 bp NcoI fragment of another isolated SSb clone, pSPB28, for the same region in pSPB37 to give pSPB39. A 1.78 kb SSb fragment was obtained by digesting PSPB39 with BamHI and BsrGI. This SSb fragment and the 4.53 kb NcoI-SmaI fragment of vector pSPB38 were rendered blunt ended by reaction with the Klenow fragment of DNA polymerase I and were ligated with each other following standard protocols (Maniatis). Bacterial transformants were screened for the presence of and the orientation of the SSb insert DNA by restriction enzyme digestion with BamHI and XhoI. This analysis led to the identification of pSPB40 which contains the 1.8 kb SSb fragment (SEQ ID NO:16) in antisense orientation with respect to the 27 kD zein promoter and the 10 kD zein 3' end. Purified pSPB40 (FIG. 4) DNA was introduced into corn callus culture cells essentially as outlined in Example 1 using 1.33 μg of pSPB40 and 0.34 μg of marker gene fragment of pML108 per bombardment. Callus samples were tested for the presence of trait gene DNA by PCR analysis and trait gene-positive samples were carried forward in the transformation regimen.

A full length sense SSb construct was also generated and introduced into corn callus tissue by the particle bombardment method. A complete copy of the SSb cDNA was first obtained using pSPB39 as the starting material. Northern blot analysis of total RNA extracted from developing endosperm indicated that the SSb transcript was approximately 3.0 kb. The remaining 5' sequence of the SSb cDNA was obtained by Rapid Amplification of cDNA Ends (RACE) using a 5' RACE System kit (Life Technologies) with some modifications to the instructions supplied by the manufacturer. Synthesis of first strand cDNA was performed at 50° using the gene specific primer OSPB104 (SEQ ID NO:17).

5'-CCATCTCCGTAGCACACACC-3' [SEQ ID NO:17]

Amplification of dI-dG-tailed cDNA was carried out with the AAP primer provided in the RACE kit and the gene specific primer OSPB105 (SEQ ID NO:18) using an Advantage GC PCR kit (Clontech).

5'-GTGCCAAGGAACCTCAACAG-3' [SEQ ID NO:18]

Re-amplification was carried out in a similar manner using the AAP primer and OSPB106 (SEQ ID NO:19).

5'-GAGGGGCATCAATGAACACA-3' [SEQ ID NO:19]

Figure 5:
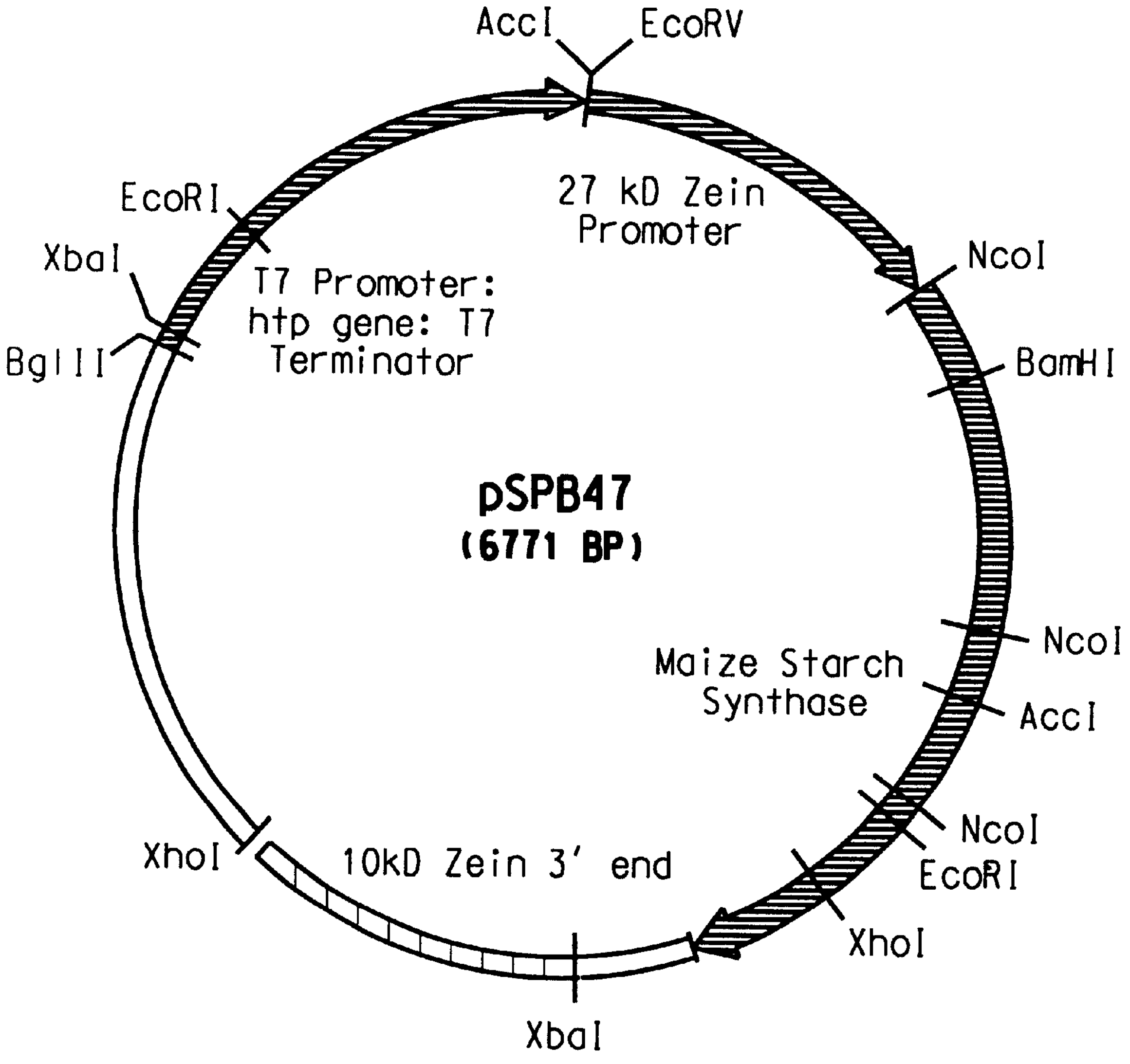
FIG. 5 presents a restriction map of plasmid pSPB47.

A full-length equivalent of the SSb cDNA, pSPB45, was created by ligating the 1346 bp segment obtained from digesting the 1485 bp 5' RACE product with Xba I and Kpn I to the 1604 bp 3' SSb region obtained from pSPB39 by digestion with Xba I and partial digestion with Kpn I. An Nco I site was introduced at the initiation codon of the coding region of pSPB45 by PCR to give pSPB46. pSPB46 was digested with BsrGI and the 5' overhang rendered blunt by an end-filling reaction with the Klenow fragment of DNA Polymerase I (Maniatis). Following partial digestion with Nco I, the 2248 bp SSb fragment (SEQ ID NO:20) was isolated and cloned into the 4.53 kb Nco I-Sma I segment of pSPB38 to give pSPB47 (FIG. 5). The plasmid pSPB47 contains the entire SSb CDNA in sense orientation surrounded by the 27 kD zein promoter and the 10 kD zein 3' end. Purified pSPB47 DNA was introduced into corn callus culture cells essentially as outlined in Example 1 using 1.43 μg of pSPB47 and 0.33 μg of the marker gene fragment of pML108 per bombardment. Callus samples were tested for the presence of trait gene DNA by PCR analysis and positive samples were advanced in the transformation regimen.

Example 7

Analysis of Starch from Transformed Corn Plants Containing the SSB Antisense Construct Starch was extracted from single seeds obtained from corn plants transformed with the SSb antisense construct as previously described. Extracted starches were enzymatically debranched as previously described and analyzed by gel permeation chromatorgraphy. Ten μL of debranched starch was injected and run through 3 narrow-bore columns (Polymer Labs, Mini-Mix C, D, E with a Mini-mix C guard column) in series at 90° and eluted with DMSO at a flow rate of 0.35 mL/min. Sampling interval was 35 minutes. A refractive index detector (Waters) was used with a computer running Waters Millenium Chromatography Manager System with GPC option (version 2.15.1, Waters Corp.) for detection and data collection and analysis, respectively. Retention times of pullulan standards (Standard 1: 380K, 100K, 23.7K, 5.8K, 666 and 180 mw, Standard 2: 853K, 186K, 48K, and 12.2K) were used to establish a $3^{rd}$ order calibration and calculate molecular weight distributions within the Millenium Software.

Figure 7:
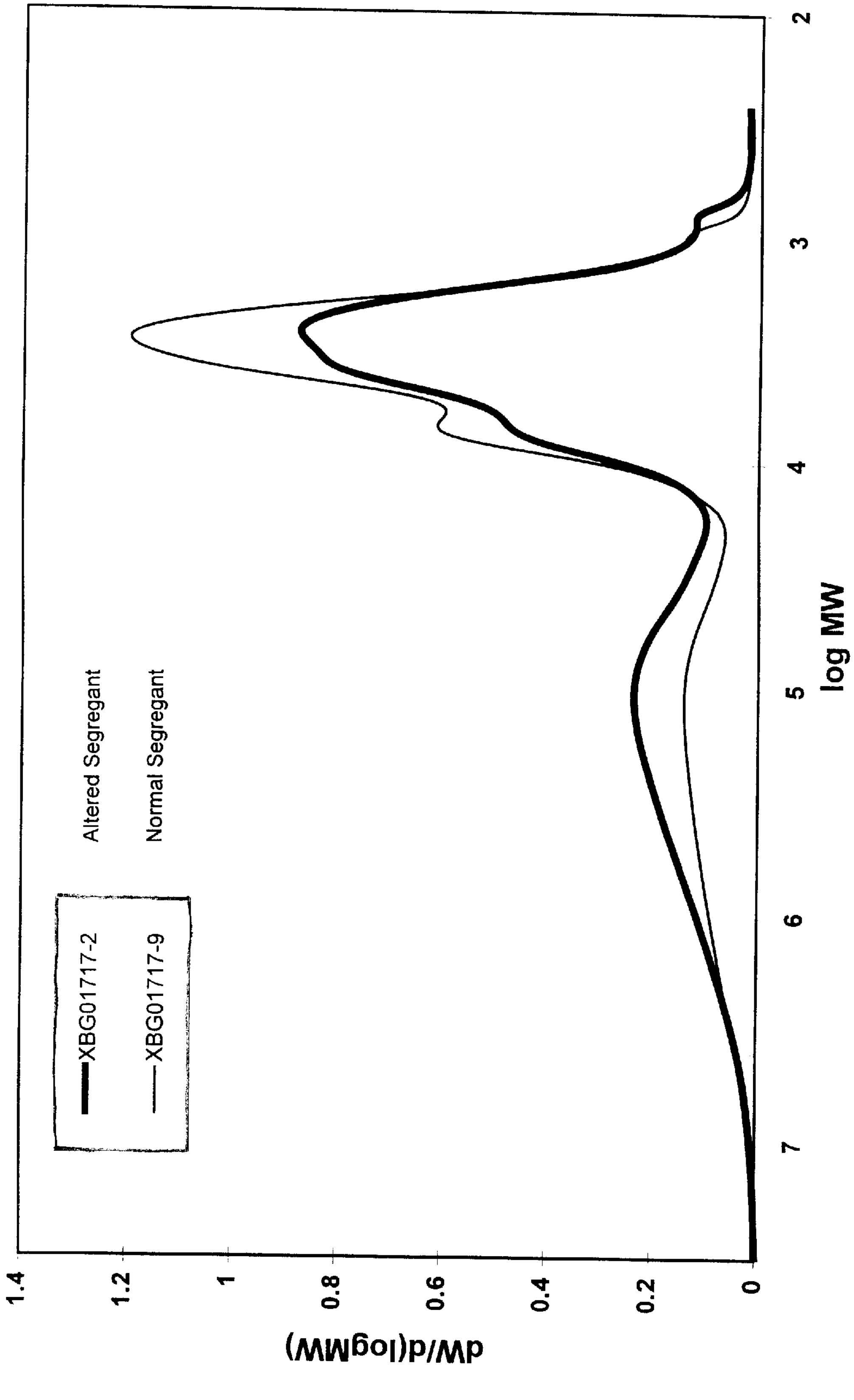
FIG. 7 presents the molecular weight distributions of debranched starches from single kernels of line S064.1.2.1 altered segregant XGB01717-2 and normal segregant XGB01717-9.

As known to those skilled in the art, the antisense phenomenon is generally not observed in every individual transgenic line. Therefore, individual kernels from multiple lines were examined and as expected some, but not all, lines possessed kernels demonstrating an altered starch phenotype. As is also known to those skilled in the art, transgenic corn plants produced by particle bombardment are typically heterozygous for the introduced transgene and will segregate the transgene in a predictable Mendelian fashion. On the selfed ear of an R0 plant the triploid endosperm, which is the tissue responsible for starch production, will segregate 1:1:1:1 for 0, 1, 2, and 3 copies of the introduced transgene, respectively. In order to have a reasonable probability of observing any of these transgene dosages 10 single kernels from line S064.1.2.1 (designated XBGO 1717-1 through XBG01717-10) were extracted for starch and the starch from each kernel was debranched and separated as described above. S064.1.2.1 produces seed that segregate starches with different types of molecular weight distributions. Some of the seed starches (XBGO1717-1, 2, 3, 4, 5, 6, and 8) produce an amylopectin (the region between log MW 3 and log MW 4.2) that is more heterogeneous than normal dent corn amylopectin, while normal dent corn shows a typical bimodal distribution (XBG01717-7, 9, and 10). FIG. 7 shows the molecular weight distributions obtained for the debranched starches obtained of two representative kernels, the normal segregant XBGO1717-9 and the altered segregant XBG01717-2. As is typical for a normal segregant, FIG. 7 shows that XBG01717-9 has a single dominant peak at log MW 3.5 and a single obvious shoulder at log MW 3.9. FIG. 7 also shows that the unusual segregant (XBG01717-2) has a split in the main peak at log MW 3.5 and a less prominent shoulder at log MW 3.9. Segregants which display this altered amylopectin structure also show an increase in the abundance of the Amylose fraction of the chromatogram (log MW>4.2) although this increase was greater in some segregants than in others. The ratio of occurrence of altered and normal amylopectin containing seeds on the segregating ear was compared to the various possible expected inheritance modes using the Chi-square ($\chi^2$) statistic. The observed frequency of 70% altered: 30% normal seeds was a reasonable fit with the simple dominance hypothesis (that 1 or more doses of the transgene were sufficient to produce altered starch structure) ($\chi^2$=0.13) or the hypothesis that 2 or more doses of the transgene were required to alter starch structure (semidominance, $\chi^2$=1.6).

Fine Structure Amylopectin Analysis of Maize SSb Anti-sense Segregants

To extend the structural comparison of the normal and SSb anti-sense starches one starch from each of the two classes described above (normal vs. altered) were compared by fluorophore taging and electrophoresis. Starch was prepared from single maize kernels, debranched and resuspended in DMSO as described above. Four μL of diluted samples were pipetted into 0.2 mL PCR reaction tubes, and 2 μL each of fluorophore (0.2 M 8-amino-1,3,6-pyrenetrisulfonic acid, trisodium salt in 15% acetic acid) and reducing agent (1 M sodium cyanoborohydride in water) were added. The tubes were tightly capped and centrifuged 2 minutes at 4000 rpm, followed by incubation at 37° for 16–18 hours. Standards were prepared with 0.2 mg/mL maltoheptaose in water and tagged in the same way as the starch samples.

Figure 8:
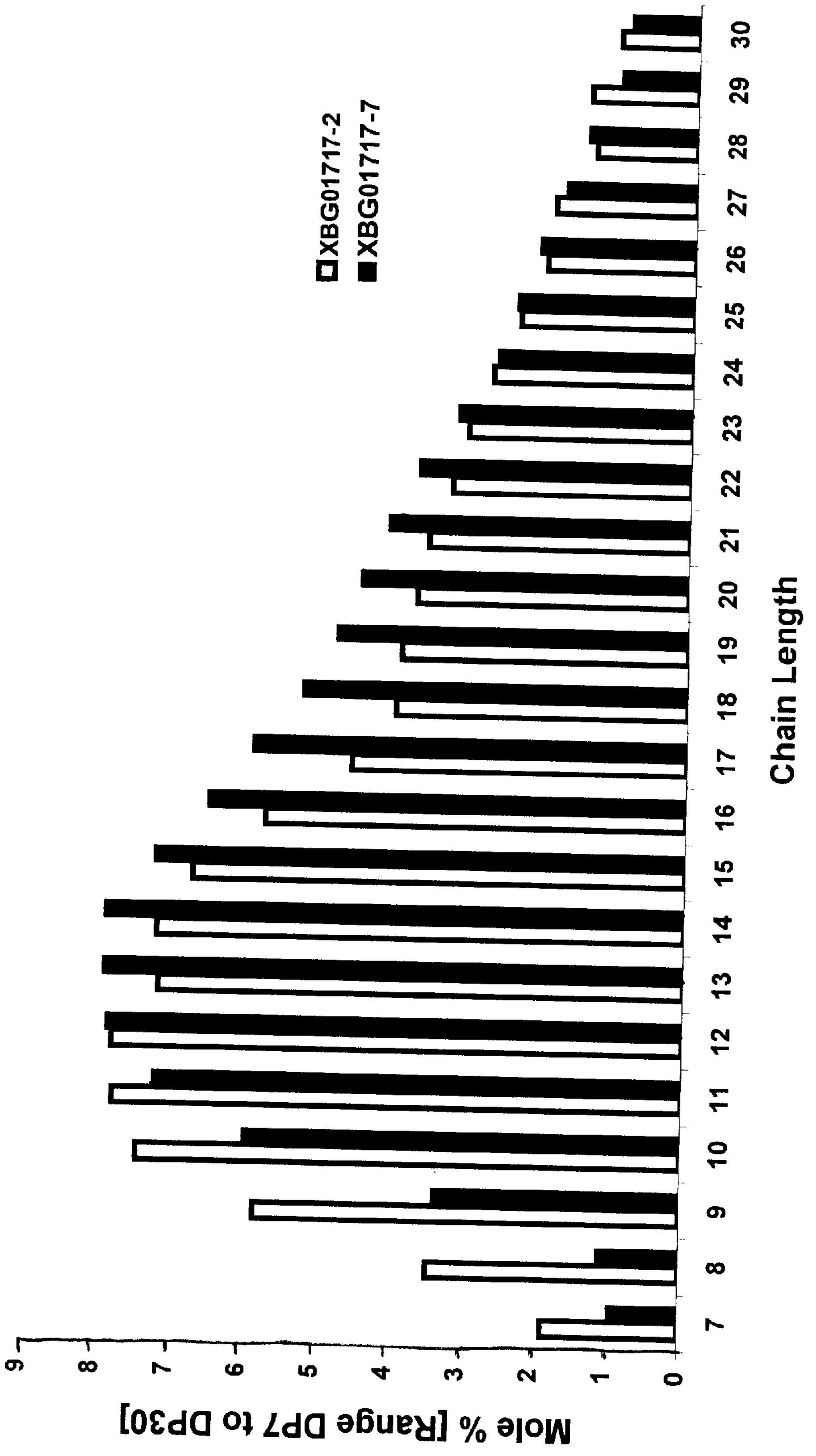
FIG. 8 presents the distribution of the relative mole percentage of chain length between DP7 and DP30 for starch derived from an altered segregating kernel and from starch derived from a non-altered segregating kernel.

Gels were poured between glass sequencing plates 36 cm well-to-read distance using 5% polyacrylamide (19:1 acrylamide:bis) in 6 M urea, 1X TBE, 0.05% ammonium persulfate and 0.07% TEMED with 0.2 mm spacers. After polymerization for 3 to 4 h, a 36 well sharkstooth comb was inserted and the wells flushed with running buffer (1×TBE). Fluorophore-tagged samples were diluted 200 to 500-fold in loading buffer (5 mM EDTA in 80% formamide with 5 mg/mL blue dextran as a visual well marker) and 1.5 μL was loaded in alternate wells. Maltoheptaose standard was used to locate the DP7 peak. Electrophoresis was performed on the Perkin-Elmer ABI 377 Gene Sequencer for 2 hours at 3000 volts at 51° and the results analyzed using ABI GeneScan software. FIG. 8 shows a graph depicting the ABI results as the relative % of each chain between DP7 and DP30.

The total moles with chains between DP7 and DP30 were calculated for XBG01717-2, an altered segregant, and for XBG01717-7, a normal segregant, and the relative mole percent of these total chains was calculated. This distribution is depicted in FIG. 8 where the altered segregant XBG01717-2 is shown to have a higher relative molar % of chains between DP7 and DP11 compared to the normal segregant XBG01717-7 which has a higher relative molar % of chains between DP12 and DP26. The relative molar % of the altered segregant is twice of that in the normal segregant for DP7 and DP8. These results show that the altered segregant is increased in very short AP chains (DP7 to DP10) and decreased in larger AP chains (DP14 to DP23).

What is claimed is:

1. A method of producing a transformed cereal crop comprising:

(a) preparing a chimeric gene comprising a nucleic acid fragment having SEQ ID NOS: 5, 6, 11, 12, 15, 16, or 20 or portions of SEQ ID NOS: 6, 11, 12, 16, or 20, said nucleic acid fragment sufficient to suppress the endogenous expression of starch synthase enzyme I or b, operably linked in sense or antisense orientation on the upstream side to a promoter that directs gene expression in a cereal crop tissue, end operably linked on the downstream side to a regulatory sequence for transcriptional termination; and (b) transforming a cereal crop with the chimeric gene of step (a), wherein expression of said chimeric gene results in alteration of the fine structure of starch derived from a grain of said transformed cereal crop when compared to the fine sancture of starch derived from a cereal crop not possessing said chimeric gene.

2. The method of claim 1 wherein the cereal crop is a corn variety.

3. The method of claim 2 wherein the nucleic acid fragment sufficient to suppress the endogenous expression of starch synthase enzyme I or b is derived from corn.

4. The method of claim 3 wherein the nucleic acid fragment is sufficient to suppress the endogenous expression of starch synthase enzyme I.

5. The method of claim 4 wherein the nucleic acid fragment comprises SEQ ID NO:5, SEQ ID NO:6, SEQ ID NO:11, or SEQ ID NO:12, or portions of SEQ ID NOS: 6, 11, or 12.

6. The method of claim 1 wherein the alteration of starch fine structure comprises alteration of the ratio of the amylose molecular component to the amylopectin molecular component of said starch.

7. The method of claim 1 wherein the alteration of starch fine structure comprises an alteration of the molecular weight distribution of the amylopectin component of said starch.

8. The method of claim 1 wherein suppression of starch synthase enzyme I results in the alteration of starch fine structure comprising an alteration in the molecular weight distribution of the amylose component of said starch.

9. The method of claim 1 wherein the nucleic acid fragment is operably linked in the sense or antisense orientation relative to a promoter that directs gene expression in corn endosperm tissue on the upstream side, and to a suitable regulatory sequence for transcriptional termination on the downstream side.

10. A corn variety prepared by the method of claim 1, or any progeny thereof, wherein said progeny comprise said chimeric gene.

11. The corn variety of claim 10 wherein the amylose molecular component of the starch isolated from the grain of said corn variety is significantly increased compared to the amylose molecular component of starch isolated from the grain of untransformed corn.

12. A cereal crop transformed with a chimeric gene comprising a nucleic acid fragment, having SEQ ID NOS: 5, 6, 11, 12, 15, 16, or 20 or portions of SEQ ID NOS: 6, 11, 12, 16, or 20, said nucleic acid fragment sufficient to suppress the endogenous expression of starch synthase enzyme I or b, operably linked in sense or antisense orientation on the upstream side to a promoter that directs gene expression in endosperm tissue, and operably linked on the downsteam side to a suitable regulatory sequence for transcriptional termination, or any progeny thereof, wherein said progeny comprise said chimeric gene.

13. The method of claim 3 wherein the nucleic acid fragment is sufficient to suppress the endogenous expression of starch synthase enzyme b.

14. The method of claim 13 wherein the nucleic acid fragment comprises SEQ ID NO: 15, SEQ ID NO:16, or SEQ ID NO:20, or portions of SEQ ID NOS: 16 or 20.

15. The cereal crop of claim 13 wherein said cereal is corn and suppression of starch synthase enzyme b results in said alteration of starch fine structure comprising raising the relative moles of the amylopectin DP7 to DP10 components of said starch.

16. A cereal crop of claim 12 wherein said cereal is a corn variety transformed with a chimeric gene comprising a nucleic acid fragment sufficient to suppress the endogenous expression of starch synthase enzyme I, operably linked in sense orientation on the upstream side to a promoter that directs gene expression in corn endosperm tissue, and operably linked on the downstream side to a suitable regulatory sequence for transcriptional termination, or any progeny thereof, wherein said progeny comprise said chimeric gene.

17. A corn variety of claim 16 wherein said nucleic acid fragment comprises SEQ ID NOS: 5, 6, 11, or 12, or portions of SEQ ID NOS: 6, 11 or 12.

18. A cereal crop of claim 12 wherein said cereal crop is a corn variety transformed with a chimeric gene comprising a nucleic acid fragment sufficient to suppress the endogenous expression of starch synthase enzyme b, operably linked in antisense orientation on the upsteam side to a promoter that directs gene expression in corn endosperm tissue, and operably linked on the downstream side to a suitable regulatory sequence for transcriptional termination, or any progeny thereof, wherein said progeny comprise said chimeric gene.

19. A corn variety of claim 18 wherein said nucleic acid fragment comprises SEQ ID NOS: 15, 16, or 20 or portions of SEQ ID NOS: 16 or 20.

20. A cereal crop of claim 12 wherein said cereal is wheat transformed with a chimeric gene comprising a nucleic acid fragment sufficient to suppress the endogenous expresson of starch synthase enzyme I, operably linked in sense orientation on the upstream side to a promoter that directs gene expression in wheat endosperm tissue, and operably linked on the downsteam side to a suitable regulatory sequence for transcriptional termination, or any progeny thereof, wherein said progeny comprise said chimeric gene.

21. A cereal crop of claim 12 wherein said cereal is wheat transformed with a chimeric gene comprising a nucleic acid fragment sufficient to suppress the endogenous expression of starch synthase enzyme b, operably linked in sense orientation on the upstream side to a promoter that directs gene expression in wheat endosperm tissue, and operably linked on the downsteam side to a suitable regulatory sequence for transcriptional termination, or any progeny thereof, wherein said progeny comprise said chimeric gene.

* * * * *